(12) United States Patent
Mayumi

(10) Patent No.: US 10,508,995 B2
(45) Date of Patent: Dec. 17, 2019

(54) THREE-DIMENSIONAL IMAGE INSPECTION DEVICE, THREE-DIMENSIONAL IMAGE INSPECTION METHOD, THREE-DIMENSIONAL IMAGE INSPECTION PROGRAM, AND COMPUTER-READABLE RECORDING MEDIUM AND RECORDING EQUIPMENT

(71) Applicant: Keyence Corporation, Osaka (JP)

(72) Inventor: Norimasa Mayumi, Osaka (JP)

(73) Assignee: Keyence Corporation, Osaka (JP)

( * ) Notice: Subject to any disclaimer, the term of this patent is extended or adjusted under 35 U.S.C. 154(b) by 203 days.

(21) Appl. No.: 15/418,790

(22) Filed: Jan. 30, 2017

(65) Prior Publication Data

US 2017/0248525 A1     Aug. 31, 2017

(30) Foreign Application Priority Data

Feb. 26, 2016   (JP) .................................. 2016-036443

(51) Int. Cl.
  *G06T 7/00*     (2017.01)
  *H04N 13/00*    (2018.01)
  (Continued)

(52) U.S. Cl.
  CPC ..... *G01N 21/8851* (2013.01); *G01N 21/8806* (2013.01); *H04N 13/275* (2018.05); *H04N 13/388* (2018.05); *G01N 2021/8887* (2013.01)

(58) Field of Classification Search
  CPC ........... G01N 21/8851; G01N 21/8806; G01N 21/9515; G01N 2021/8887; H04N 13/388; H04N 13/275
  (Continued)

(56) References Cited

U.S. PATENT DOCUMENTS 5,812,269 A  *  9/1998  Svetkoff ................. G01B 11/24
                                            250/559.23
2014/0071243 A1* 3/2014  Nakatsukasa .......... G01B 11/25
                                            348/46
(Continued)

FOREIGN PATENT DOCUMENTS

JP         2015-031539          2/2015
JP         2015-031540          2/2015

*Primary Examiner* — Susan E. Hodges
(74) *Attorney, Agent, or Firm* — Kilyk & Bowersox, P.L.L.C.

(57) ABSTRACT

The three-dimensional image inspection device includes a composed image generation part configured to compose first three-dimensional data and second three-dimensional data, and generate a three-dimensional composed image having information in a height direction, a composition mode selection part configured to enable a first composition mode and a second composition mode to be selected, the first composition mode being a mode in which the three-dimensional composed image is generated, based on the three-dimensional data measured by both a first light projecting/receiving part and a second light projecting/receiving part with respect to respective pixels configuring the three-dimensional composed image, and the second composition mode being a mode in which the three-dimensional composed image is generated, based on the three-dimensional data measured by any one or both of the first light projecting/receiving part and the second light projecting/receiving part with respect to the respective pixels.

11 Claims, 16 Drawing Sheets

(51) Int. Cl.
*G01B 11/24* (2006.01)
*G01N 21/88* (2006.01)
*H04N 13/275* (2018.01)
*H04N 13/388* (2018.01)

(58) Field of Classification Search
USPC .......................................................... 348/47
See application file for complete search history.

(56) References Cited

U.S. PATENT DOCUMENTS

| | | | |
|---|---|---|---|
| 2015/0022638 A1* | 1/2015 | Saeki | G06T 7/0004 348/46 |
| 2016/0196643 A1* | 7/2016 | Bendall | G06T 7/50 382/108 |
| 2017/0249727 A1 | 8/2017 | Mayumi | |

* cited by examiner

HEI2'

HEI1'

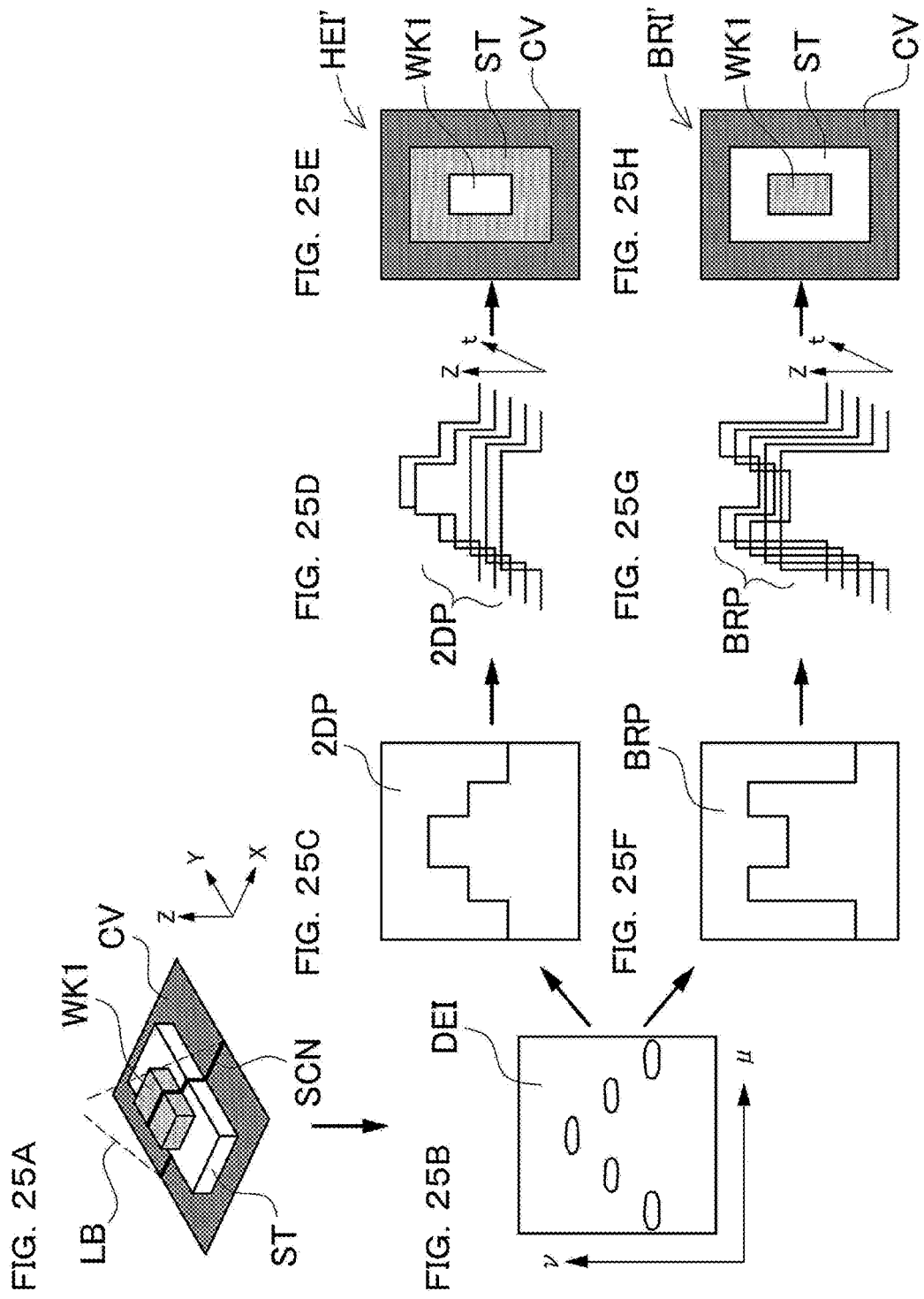

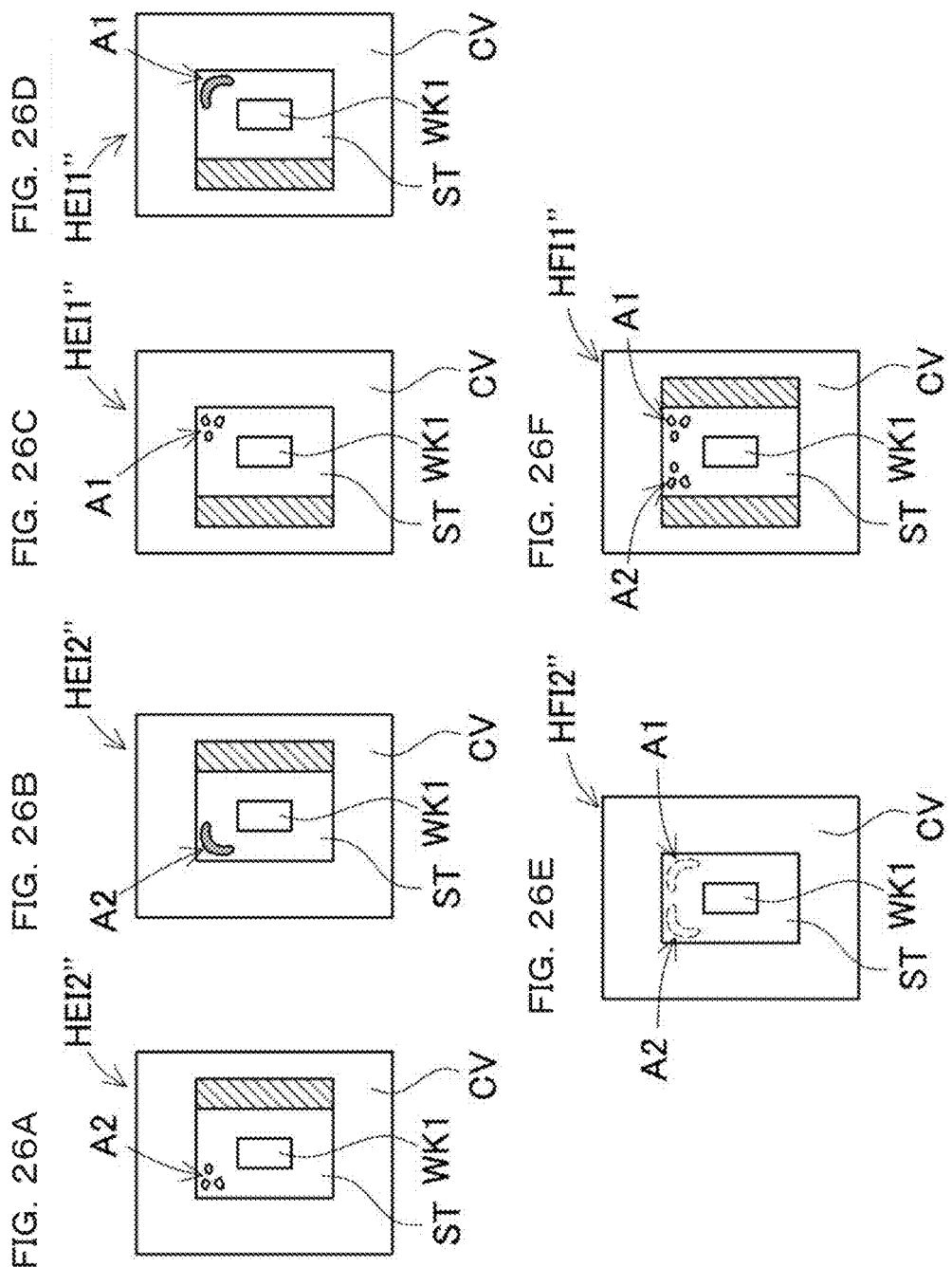

THREE-DIMENSIONAL IMAGE INSPECTION DEVICE, THREE-DIMENSIONAL IMAGE INSPECTION METHOD, THREE-DIMENSIONAL IMAGE INSPECTION PROGRAM, AND COMPUTER-READABLE RECORDING MEDIUM AND RECORDING EQUIPMENT

CROSS-REFERENCE TO RELATED APPLICATIONS

The present application claims foreign priority based on Japanese Patent Application No. 2016-036443, filed Feb. 26, 2016, the contents of which is incorporated herein by reference.

BACKGROUND OF THE INVENTION

1. Field of the Invention

The invention relates to a three-dimensional image inspection device, a three-dimensional image inspection method, a three-dimensional image inspection program, and a computer-readable recording medium, or recording equipment.

2. Description of Related Art

There have been utilized three-dimensional image inspection devices that conduct inspection of presence or absence of a surface flaw, an outer appearance shape, reading of printed characters or the like in a workpiece (an inspection object or a subject). The above-described three-dimensional image inspection devices have applied necessary illumination to the workpiece to capture an image, and have performed image processing such as edge detection for obtained image data to determine quality or the like, based on a result.

There has been known a device that continuously acquires profile data, which is a two-dimensional cross-sectional shape of a workpiece, to configure data of a three-dimensional shape of the workpiece by moving a two-dimensional profile measuring instrument by an optical cutting method or by an optical scanning method relatively to the workpiece, and creates a height image changing pixel values in accordance with a distance from a camera to the workpiece to inspect quality of the workpiece (e.g., refer to Japanese Unexamined Patent Application Publication No. 2015-31540).

In the two-dimensional profile measuring instrument using a principle of triangulation, in the measurement principle, there disadvantageously exists a region where measurement is disabled because light does not reach the region (or a camera is disabled to capture an image) or the like.

Moreover, influence by multiple reflection of light on a workpiece surface, a shade boundary on the workpiece surface, specular reflection or the like may cause noise, may result in low-reliability data, or may make it hard to obtain sufficient inspection accuracy.

SUMMARY OF THE INVENTION

The invention is achieved in light of the above-described circumstances, and an object of the invention is to provide a three-dimensional image inspection device, a three-dimensional image inspection method, a three-dimensional image inspection program, and a computer-readable recording medium, or recording equipment that reduce a dead angle, and enable inspection to be enhanced in reliability.

According to one embodiment of the invention, a three-dimensional image inspection device is a three-dimensional image inspection device for conducting outer appearance inspection, based on height information of an inspection object, the three-dimensional image inspection device including a first light projecting/receiving part configured to apply measurement light to the inspection object at a first incident angle, and receive reflected light reflected from the inspection object at a first reflection angle, a second light projecting/receiving part configured to apply measurement light to the inspection object at a second incident angle, and receive reflected light reflected from the inspection object at a second reflection angle, a three-dimensional data generation part configured to generate first three-dimensional data, based on first light receiving amount data obtained from the first light projecting/receiving part, and generate second three-dimensional data, based on second light receiving amount data obtained from the second light projecting/receiving part in accordance with a principle of triangulation, a composed image generation part configured to compose the first three-dimensional data and the second three-dimensional data, and generate a three-dimensional composed image having information in a height direction, a display part configured to display the three-dimensional composed image composed by the composed image generation part, a composition mode selection part configured to enable a first composition mode and a second composition mode to be selected when the composed image generation part generates the three-dimensional composed image, the first composition mode being a mode in which the three-dimensional composed image is generated, based on the three-dimensional data measured by both the first light projecting/receiving part and the second light projecting/receiving part with respect to respective pixels configuring the three-dimensional composed image, and the second composition mode being a mode in which the three-dimensional composed image is generated, based on the three-dimensional data measured by any one or both of the first light projecting/receiving part and the second light projecting/receiving part with respect to the respective pixels configuring the three-dimensional composed image, and an inspection part configured to conduct the outer appearance inspection of the inspection object, based on the three-dimensional composed image composed by the composed image generation part. The above-described configuration enables the user to select whether the measurement of a dead angle region is given priority or the reliability of the measurement value is given priority in accordance with the inspection object or an inspection type.

According to another embodiment of the invention, in the three-dimensional image inspection device, the first composition mode selected by the composition mode selection part can be a reliability priority mode that gives priority to the three-dimensional data having high reliability, based on the pixels measured by both the first light projecting/receiving part and the second light projecting/receiving part, and the second composition mode can be a measurement priority mode that complements the pixels measured by only any one of the first light projecting/receiving part and the second light projecting/receiving part, using the three-dimensional data measured by the other light projecting/receiving part. With the above-described configuration, in addition to the measurement priority mode in which the pixels that cannot be measured by only one of the light projecting/receiving parts due to the dead angle or the like can be complemented, using the three-dimensional data that can be measured by the other, with respect to the pixels that can be measured by both the light projecting/receiving parts as well, the three-dimensional data having higher reliability is preferentially used, which can implement the three-dimensional image inspection enhanced in reliability of the measurement.

According to still another embodiment of the invention, in the three-dimensional image inspection device, the composed image generation part can perform noise removal processing of the three-dimensional composed image in the first composition mode, and dead angle removal processing of the three-dimensional composed image in the second composition mode.

According to still another embodiment of the invention, in the three-dimensional image inspection device, the first incident angle and the second incident angle, or the first reflection angle and the second reflection angle can be different angles.

According to still another embodiment of the invention, in the three-dimensional image inspection device, the composed image generation part can determine a value of a pixel with respect to which any one of the first three-dimensional data and the second three-dimensional data is invalid data to be an invalid pixel in the first composition mode, and a value of a pixel with respect to which both the first three-dimensional data and the second three-dimensional data are invalid data to be an invalid pixel in the second composition mode.

According to still another embodiment of the invention, in the three-dimensional image inspection device, the composed image generation part can determine a value of a pixel with respect to which both of the first three-dimensional data and the second three-dimensional data are valid data to be a valid pixel in the first composition mode, and a value of a pixel with respect to which any one of the first three-dimensional data and the second three-dimensional data is valid data to be a valid pixel in the second composition mode.

According to still another embodiment of the invention, in the three-dimensional image inspection device, the first light projecting/receiving part and the second light projecting/receiving part can each output luminance information of the inspection object together with the three-dimensional data.

According to still another embodiment of the invention, in the three-dimensional image inspection device, the luminance information can be luminance profiles, and the luminance profiles can be joined to generate a luminance image.

According to still another embodiment of the invention, in the three-dimensional image inspection device, the composed image generation part can decide reliability of the first three-dimensional data and the second three-dimensional data, based on the luminance information in the first composition mode.

According to still another embodiment of the invention, in the three-dimensional image inspection device, when the height information is obtained in both the corresponding pixels of the first three-dimensional data and the second three-dimensional data, the composed image generation part can set the data having high reliability as the height information of the relevant pixel, based on the luminance information.

According to still another embodiment of the invention, in the three-dimensional image inspection device, when a difference between luminance values of the corresponding pixels is larger than a predetermined threshold, it can be determined that the reliability of the three-dimensional data of the pixel having the smaller luminance value is lower.

According to still another embodiment of the invention, the three-dimensional image inspection device can further include a luminance image generation part configured to compose first luminance data obtained by the first light projecting/receiving part, and second luminance data obtained by the second light projecting/receiving part and generate a luminance composed image. The above-described configuration enables the inspection using the luminance composed image.

According to still another embodiment of the invention, in the three-dimensional image inspection device, when the height information is obtained with respect to both the corresponding pixels of the two pieces of three-dimensional data in the first composition mode, the data having higher reliability can be preferentially employed.

According to still another embodiment of the invention, in the three-dimensional image inspection device, when the height information is obtained in both the corresponding pixels of the first three-dimensional data and the second three-dimensional data, the composed image generation part can average the two pieces of height information.

According to still another embodiment of the invention, in the three-dimensional image inspection device, when a difference in the height information between the corresponding pixels of the first three-dimensional data and the second three-dimensional data is a predetermined position, the composed image generation part can determine that the relevant pixel has low reliability. With the above-described configuration, since divergence of the height information obtained by the first three-dimensional data and the second three-dimensional data is large, and it can be considered that any of them includes an error, the relevant pixel is treated as a pixel having low reliability, by which a decrease in measurement accuracy can be avoided.

According to still another embodiment of the invention, the three-dimensional image inspection device can further include a storage part configured to store a position adjustment parameter that prescribes a correspondence relation in a coordinate space between the first three-dimensional data and the second three-dimensional data generated by the three-dimensional data generation part, wherein the composed image generation part can compose the first three-dimensional data and the second three-dimensional data, based on the position adjustment parameter stored in the storage part, and can generate the three-dimensional composed image having the information in the height direction. With the above-described configuration, a deviation amount beforehand calculated by calibration between the first light projecting/receiving part and the second light projecting/receiving part is stored, which enables the composition to be performed based on this deviation amount at the operation time, so that an advantage of accelerating the processing can be obtained.

According to still another embodiment of the invention, in the three-dimensional image inspection device, the display part can display, side by side, the first three-dimensional composed image composed in the first composition mode and the second three-dimensional composed image composed in the second composition mode by the composed image generation part. With the above-described configuration, the respective three-dimensional composed images obtained in the first composition mode and the second composition mode are displayed in one screen, which makes it easier for the user to visually compare which processing is more desirable.

According to still another embodiment of the invention, the display part can display the first three-dimensional data and the second three-dimensional data side by side. With the above-described configuration, the two pieces of three-dimensional data obtained by the first light projecting/ receiving part and the second light projecting/receiving part are displayed in one screen, which makes it easier for the user to compare these.

According to still another embodiment of the invention, in the three-dimensional image inspection device, the three-dimensional composed image composed by the composed image generation part can be a height image in which the information in the height direction is a pixel value of each of the pixels.

According to one embodiment of the invention, a three-dimensional image inspection method is a three-dimensional image inspection method for conducting an outer appearance inspection, based on three-dimensional composed image having height information of an inspection object, the method including the steps of promoting a user to select any of a first composition mode in which noise removal processing of the three-dimensional composed image is performed, and a second composition mode in which dead angle removal processing of the three-dimensional composed image is performed, applying measurement light to the inspection object at a first incident angle, and receiving reflected light reflected from the inspection object at a first reflection angle by a first light projecting/receiving part, and meanwhile, applying measurement light to the same inspection object at a second incident angle, and receiving reflected light reflected from the inspection object at a second reflection angle by a second light projecting/receiving part, and in accordance with a principle of triangulation, generating first three-dimensional data, based on first light receiving amount data obtained from the first light projecting/receiving part, and meanwhile, generating second three-dimensional data, based on second light receiving amount data obtained from the second light projecting/receiving part, when the first three-dimensional data and the second three-dimensional data are composed to generate a three-dimensional composed image having information in a height direction, in accordance with the selection of the first composition mode and the second composition mode, generating the three-dimensional composed image, based on the three-dimensional data measured by both the first light projecting/receiving part and the second light projecting/receiving part with respect to respective pixels configuring the three-dimensional composed image when the first composition mode is selected, and generating the three-dimensional composed image, based on the three-dimensional data measured by any one or both of the first light projecting/receiving part and the second light projecting/receiving part with respect to the respective pixels when the second composition mode is selected, causing a display part to display the three-dimensional composed image composed by a composed image generation part, and conducting the outer appearance inspection of the inspection object, based on the composed three-dimensional composed image. This enables the user to select whether measurement of a dead angle region is given priority or reliability of a measurement value is given priority in accordance with the inspection object and the inspection type.

BRIEF DESCRIPTION OF THE DRAWINGS

FIG. 25A is a perspective view showing how the workpiece in FIG. 6A is placed on a stand and conveyed, FIG. 25B is a schematic view showing a light receiving image obtained by applying a laser beam to the inspection object in FIG. 25A and detecting reflected light, FIG. 25C is a schematic view of a two-dimensional profile obtained from FIG. 25B, FIG. 25D is a schematic view showing a state where the two-dimensional profiles in FIG. 25C are composed at respective scanning positions, FIG. 25E is a schematic view showing the height image obtained by composing the two-dimensional profiles in FIG. 25D, FIG. 25F is a schematic view showing a luminance profile obtained from FIG. 25B, FIG. 25G is a state where the luminance profiles are composed at the respective scanning positions, and FIG. 25H is a schematic view showing the luminance image obtained by composing the luminance profiles in FIG. 25G; and FIG. 26A is a view showing the second height image of the inspection object in FIG. 25A, FIG. 26B is a view showing a second luminance image, FIG. 26C is a view showing the first height image, FIG. 26D is a first luminance image, FIG. 26E is a view showing a second height composed image, and FIG. 26F is a view showing a first height composed image.

DETAILED DESCRIPTION OF PREFERRED EMBODIMENTS

Figure 1:
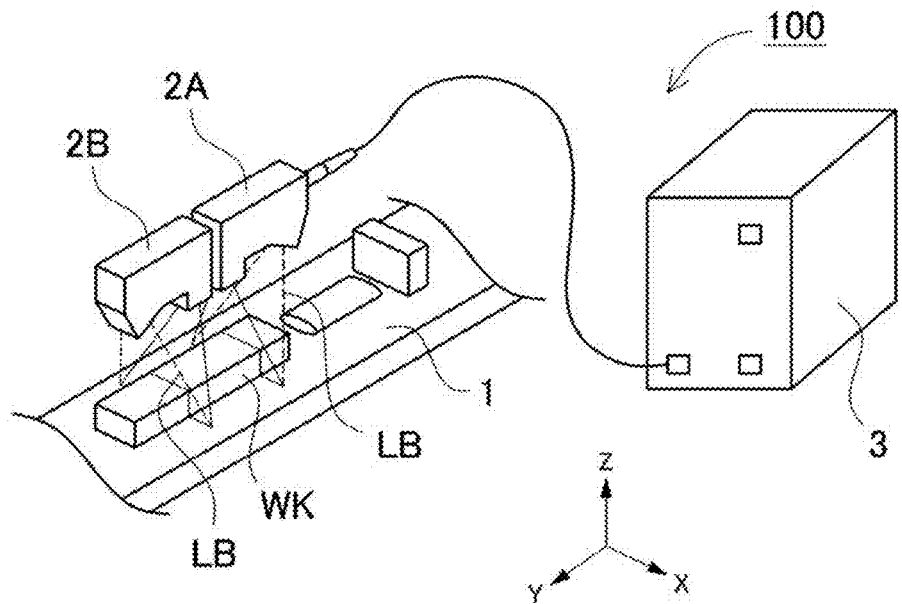
FIG. 1 is a perspective view showing an outer appearance of a three-dimensional image inspection device according to a first embodiment of the invention.

Hereinafter, embodiments of the invention will be described with reference to the drawings. However, the embodiments described below are illustrations for embodying technical ideas of the invention, and the invention is not specified by the following. Moreover, the specification does not specify members described in the scope of the claims to members of the embodiments. Especially, unless specific descriptions are given, dimensions, materials, shapes, relative dispositions and the like of components described in the embodiments are not intended to limit the scope of the invention thereto, but are only explanatory examples. Sizes, positional relations and the like of the members shown in the respective drawings may be emphasized for clarification of description. In the following description, the same names and reference numerals denote the same or equivalent members, and detailed description is omitted as needed. Furthermore, as to respective elements constituting the invention, an aspect may be employed in which a plurality of elements are configured by a same member, and the one member is used for the plurality of elements, or a function of one member can be shared and realized by a plurality of members.

First Embodiment

Figure 2:
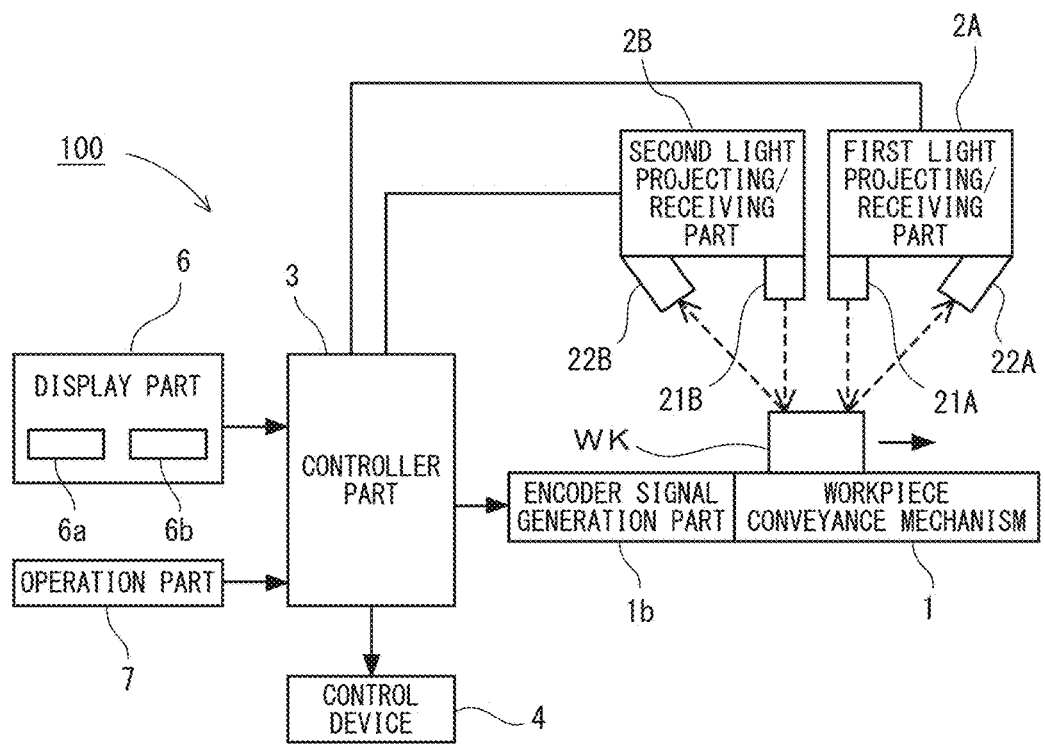
FIG. 2 is a block diagram showing the three-dimensional image inspection device in FIG. 1.
Figure 3:
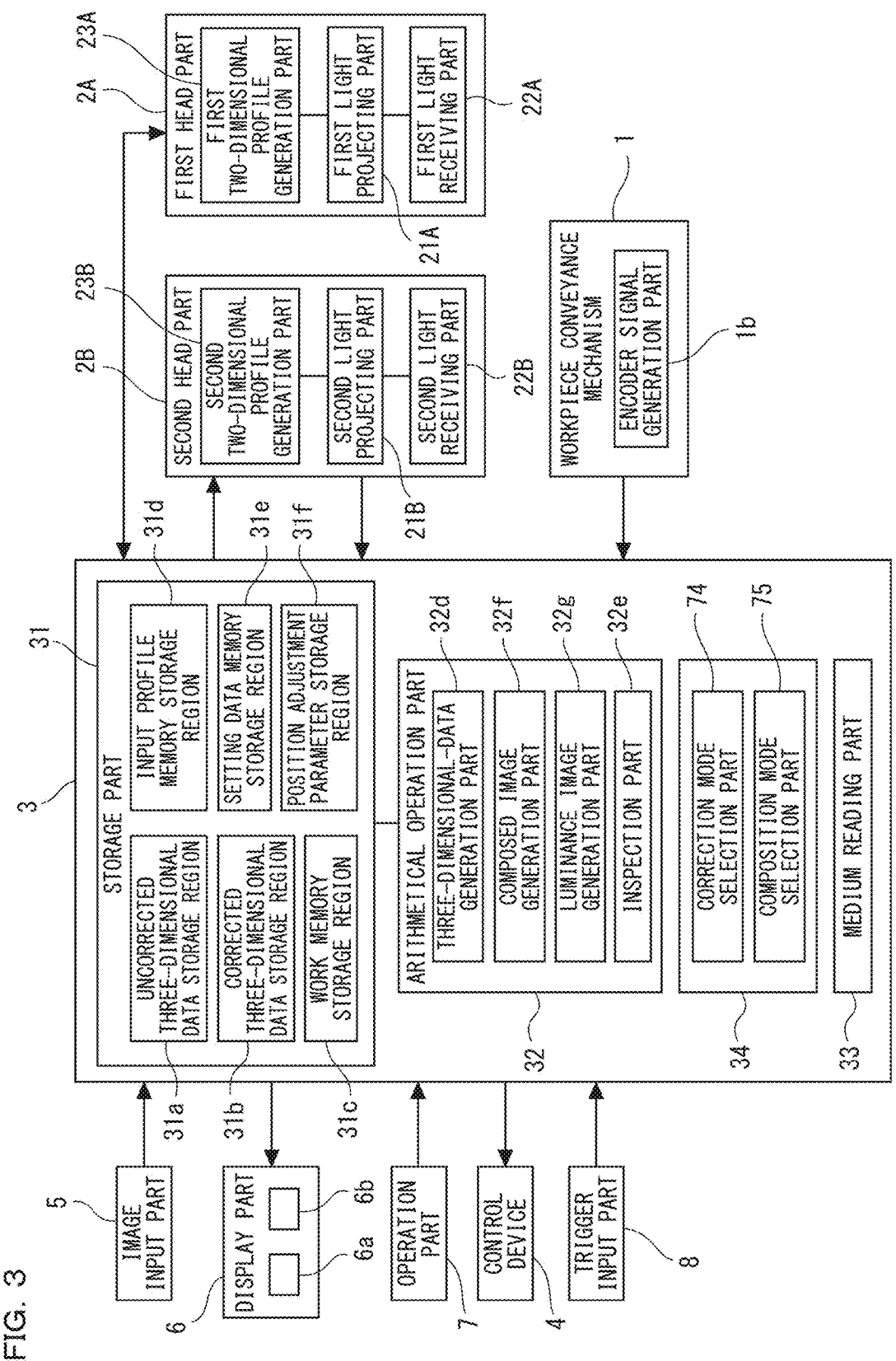
FIG. 3 is a detailed functional block diagram of the three-dimensional image inspection device in FIG. 1.

An outer appearance of a three-dimensional image inspection device according to a first embodiment of the invention is shown in FIG. 1, a block diagram is shown in FIG. 2, and a more detailed functional block diagram is shown in FIG. 3. A three-dimensional image inspection device 100 shown in these diagrams inspects, by image processing, the outer appearance of an inspection object (a workpiece WK) conveyed on a workpiece conveyance mechanism 1. This three-dimensional image inspection device 100 includes a first head part 2A and a second head part 2B that each capture an image of the workpiece WK, and a controller part 3 that applies the image processing to the images obtained by the first head part 2A and the second head part 2B. The controller part 3 conducts outer appearance inspection to each of the images having height information by the image processing to output an inspection result. The outer appearance inspection is a production inspection executed, using the image processing result of the workpiece WK, and includes dimension inspection for measuring dimensions of the workpiece WK, non-defective product inspection for determining whether or not the workpiece WK is a non-defective product, and the like. The workpiece conveyance mechanism 1 is a line such as a conveyer controlled by a control device 4 such as a programmable logic controller (PLC).

The three-dimensional image inspection device 100 includes the first head part 2A, the second head part 2B, and the controller part 3, as shown in the block diagram of FIG. 3. To the controller part 3 are connected an image input part 5, a display part 6, an operation part 7, the control device 4, and a trigger input part 8. Moreover, a signal from an encoder signal generation part 1b of the workpiece conveyance mechanism 1 is inputted to the controller part 3, so that it can be grasped that the workpiece WK is being conveyed by the workpiece conveyance mechanism 1, or that the conveyance of the workpiece WK is stopped. The encoder signal generation part 1b is, for example, a rotary encoder or the like provided at a rotating shaft of a conveyer for the signal indicating an operation state of the workpiece conveyance mechanism 1. The image input part 5 is a unit with a connector. The image input part 5 is not limited to an aspect in which the image input part is externally attached, but an aspect in which the image input part is built in the controller part 3 may be employed.

The trigger input part 8 is a member to indicate imaging timing of the workpiece WK to the controller part 3. For example, a trigger signal from a photoelectronic sensor disposed on the workpiece conveyance mechanism 1 is received by the trigger input part 8, by which it is detected that the workpiece WK has been conveyed, so that timing when processing such as the imaging, and the outer appearance inspection is performed can be set.

(Operation Part 7)

The operation part 7 is a member to perform various operations and settings to the controller part 3. A keyboard, a console, a pointing device such as a mouse can be utilized.

(Display Part 6)

Figure 4:
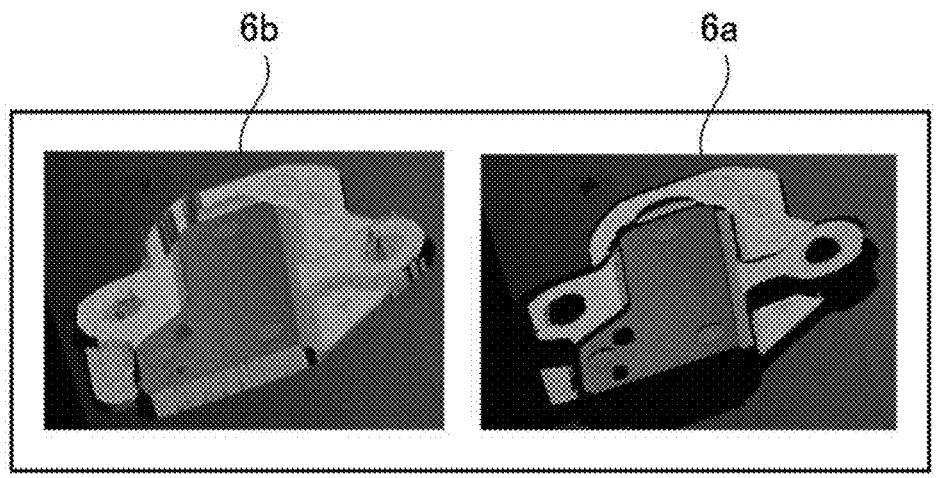
FIG. 4 is an image view showing an example in which a first three-dimensional composed image display region and a second three-dimensional composed image display region are displayed side by side in a display part.

The display part 6 is a member to display obtained three-dimensional data or height image, a three-dimensional composed image, a luminance composed image and a result of the outer appearance inspection, a setting screen for making various settings, setting values inputted to this setting screen from the operation part 7, and so on. The above-described display part 6 is a display of an LCD, a CRT, an organic EL or the like. Moreover, in the case where the display part 6 includes a touch panel, it can function as both the operation part and the display part. Moreover, this display part 6 has a first three-dimensional composed image display region 6a to display a first three-dimensional composed image, which is composed in a first composition mode described later, and a second three-dimensional composed image display region 6b to display a second three-dimensional composed image, which is composed in a second composition mode. Furthermore, as shown in FIG. 4, the first three-dimensional composed image display region 6a and the second three-dimensional composed image display region 6b are enabled to be displayed side by side in one screen, which makes it easy for a user to evaluate which processing is more suitable for an outer appearance inspection purpose while comparing these images.

Figure 5:
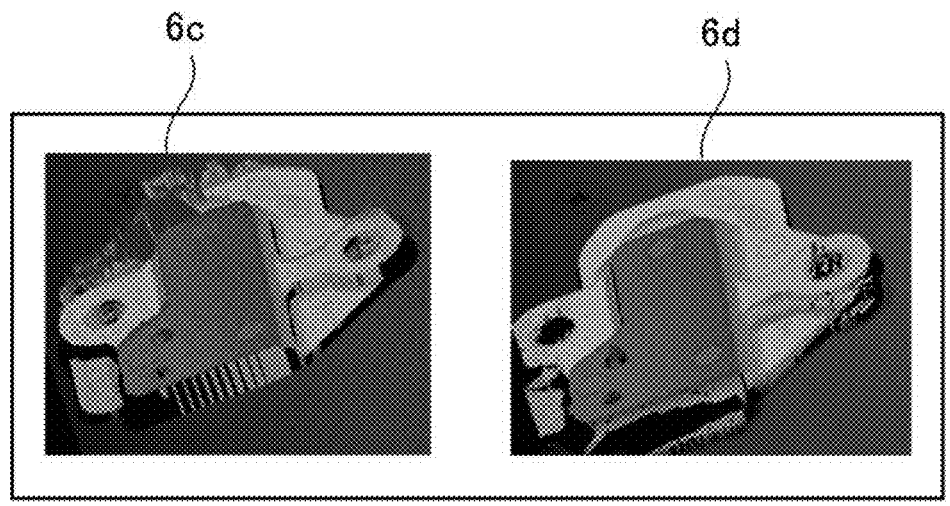
FIG. 5 is an image view showing an example in which a first three-dimensional data display region and a second three-dimensional data display region are displayed side by side in the display part.

In addition, as shown in FIG. 5, the display part 6 is also enabled to display, side by side, a first three-dimensional data display region 6c to display first three-dimensional data, and a second three-dimensional data display region 6d to display second three-dimensional data. Thereby, two pieces of three-dimensional data obtained by a first light projecting/receiving part and a second light projecting/receiving part are displayed in one screen, which makes it easy for the user to visually compare the two pieces of data. Further, in a state where the first three-dimensional data display region 6c and the second three-dimensional data display region 6d are displayed in the display part 6 side by side, the first three-dimensional composed image display region 6a and the second three-dimensional composed image display region 6b may be simultaneously displayed. Alternatively, the invention is not limited to the configuration in which these regions are displayed simultaneously, but these regions may be switched over to be displayed. For example, in the display part 6, a state where the first three-dimensional data, the second three-dimensional data, and the first three-dimensional composed image are displayed side by side, and a state where the first three-dimensional data, the second three-dimensional data, and the second three-dimensional composed image are displayed side by side can be freely switched over. This make it easy to compare the three-dimensional composed images obtained in the first composition mode and the second composition mode.

(Controller Part 3)

The controller part 3 shown in FIG. 3 includes a storage part 31, an arithmetical operation part 32, a setting part 34, and a medium reading part 33. The arithmetical operation part 32 includes a three-dimensional data generation part 32d, a composed image generation part 32f, a luminance image generation part 32g, and an inspection part 32e. The storage part 31 is a member to store various types of image data and setting data, and includes an uncorrected three-dimensional data storage region 31a, and a corrected three-dimensional data storage region 31b, a workpiece memory storage region 31c, an input profile memory storage region 31d, a setting data memory storage region 31e, a position adjustment parameter storage region 31f, and the like. The medium reading part 33 is a member to read or write in a portable medium, and a recording medium, a semiconductor memory or the like, which is standardized, such as a USB memory (product name), and an SD card (product name) is connected to enable the reading and writing of the data. Moreover, the configuration may be such that the data is received and transmitted with respect to external recording equipment through wireless connection or network connection.

The three-dimensional data generation part 32d is a member to generate the three-dimensional data of the inspection object from a plurality of two-dimensional profiles. The inspection part 32e is a member to conduct the outer appearance inspection of the inspection object, based on the three-dimensional data generated by the three-dimensional data generation part 32d.

The composed image generation part 32f is a member to compose the first three-dimensional data and the second three-dimensional data, and generate the three-dimensional composed image having information in a height direction. Moreover, the composed image generation part 32f can also generate the three-dimensional composed image, based on position adjustment parameters stored in the storage part 31.

The luminance image generation part 32g is a member to compose first luminance data obtained by the first light projecting/receiving part, and second luminance data obtained by second light projecting/receiving part, and generate the luminance composed image.

The setting part 34 includes a correction mode selection part 74 and a composition mode selection part 75.

The composition mode selection part 75 is a member to select the first composition mode and the second composition mode when the composed image generation part 32f generates the three-dimensional composed image. In the first composition mode, the three-dimensional composed image is generated, based on the three-dimensional data measured by both the first light projecting/receiving part and the second light projecting/receiving part with respect to respective pixels configuring the three-dimensional composed image, and in the second composition mode, the three-dimensional composed image is generated, based on the three-dimensional data measured by any one or both of the first light projecting/receiving part and the second light projecting/receiving part with respect to the above-described respective pixels.

The arithmetical operation part 32 can be implemented, for example, by a microprocessor (an MPU), a CPU, an LSI, a gate array such as an FPGA and an ASIC, hardware and software of a DSP and the like, or by mixing these. Moreover, the respective components need not be the same as those in the configuration shown in FIG. 3, and a component having substantially the same function and a component having the functions of the plurality of elements in the configuration shown in FIG. 3 are included in the invention.

Using the above-described scanning type three-dimensional image inspection device 100, the outer appearance inspection of the workpiece WK conveyed by the workpiece conveyance mechanism 1 is conducted.

(First Head Part 2A)

The first head part 2A is a member to measure the two-dimensional profile of the workpiece WK, and is one form of the first light projecting/receiving part. As shown in a block diagram of FIG. 3, the first head part 2A includes a first light projecting part 21A to apply measurement light to the workpiece WK relatively moved in one direction, a first light receiving part 22A to detect reflected light that is applied to the workpiece WK from the first light projecting part 21A and reflected, and a first two-dimensional profile generation part 23A to generate the two-dimensional profile indicating a cross-sectional shape of the workpiece WK, based on detection data obtained by the first light receiving part 22A. In the specification, the "height direction" is used as a distance direction between the first head part 2A (exactly, the first light receiving part 22A) and the workpiece WK.

Figure 6B:
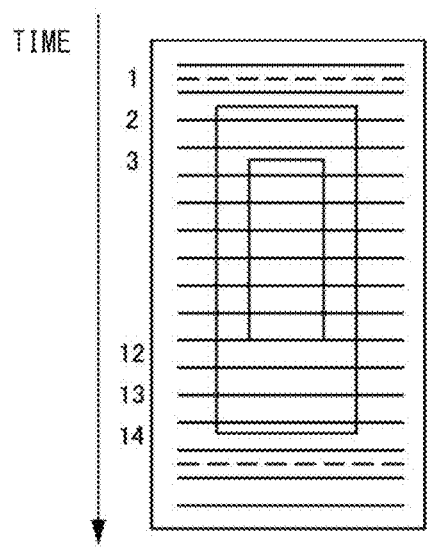
FIG. 6B is a plan view of the workpiece showing scanning positions.
Figure 6C:
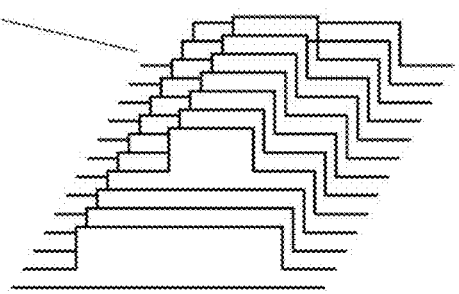
FIG. 6C is a schematic view in which two-dimensional profiles obtained at the respective scanning positions in FIG. 6B are composed to generate three-dimensional data.
Figure 6A:
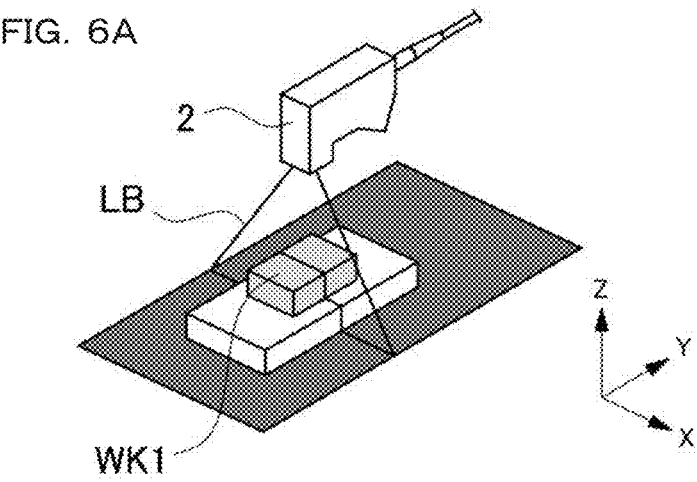
FIG. 6A is a perspective view showing a state where a workpiece is scanned by a light projecting/receiving part.

In this first head part 2A, as shown in FIG. 6A, the first light projecting part 21A applies a wide laser beam LB in an X-axis direction (a width direction) to a workpiece WK1 conveyed in a Y-axis direction (a feeding direction) and receives reflected light by the first light receiving part 22A, so that the first two-dimensional profile generation part 23A creates the two-dimensional profile as data indicating the two-dimensional cross-sectional shape of the workpiece WK. At this time, the workpiece WK is virtually cut along a cut surface parallel to an XZ plane, and an outer shape (an outer edge) of the cut surface serves as the two-dimensional profile (FIGS. 6B and 6C). The two-dimensional profile is generally a set of distances from the first head part 2A to measurement points of the workpiece WK (distances in a Z-axis direction), that is, a set of distances of the plurality of measurement points lined along the X-axis direction.

For the first head part 2A, a laser displacement meter of a line projection type is used. Specifically, the first head part 2A includes a light projecting element that emits the laser beam LB or the like as the first light projecting part 21A, and a light receiving element (a line sensor or a two-dimensional imaging element) such as a CCD, and a CMOS as the first light receiving part 22A. Furthermore, the first head part 2A includes an optical system such as lenses to guide the applied light and the reflected light. This first head part 2A can also be considered as a camera to image the workpiece WK.

(Second Head Part 2B)

The second head part 2B can employ an almost similar configuration to that of the above-described first head part 2A. That is, the second head part 2B is one form of the second light projecting/receiving part, and as shown in the block diagram of FIG. 3, the second head part 2B includes a second light projecting part 21B to apply measurement light to the workpiece WK relatively moved in one direction, a second light receiving part 22B to detect reflected light that is applied to the workpiece WK from the second light projecting part 21B and reflected, and a second two-dimensional profile generation part 23B to generate the two-dimensional profile indicating the cross-sectional shape of the workpiece WK, based on detection data obtained by the second light receiving part 22B.

Second Embodiment

Figure 7:
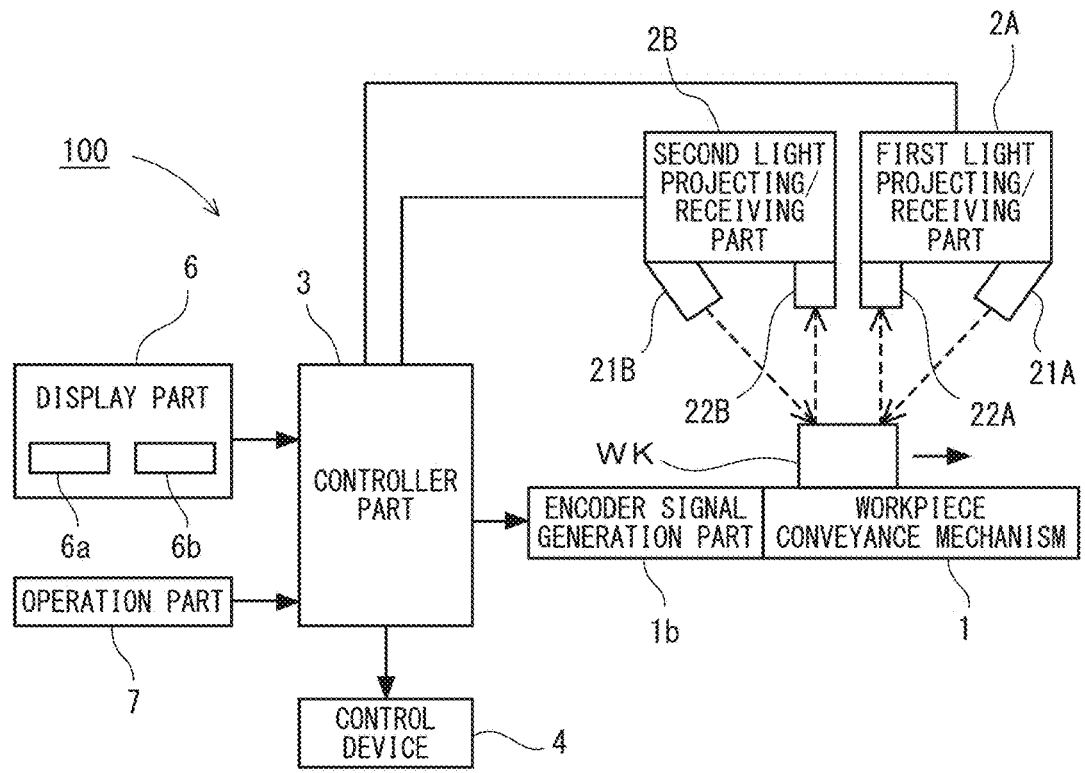
FIG. 7 is a perspective view showing an outer appearance of a three-dimensional image inspection device according to a second embodiment.

In the example of FIG. 2, a first incident angle of the first head part 2A and a second incident angle of the second head part 2B are almost equal, and a first reflection angle and a second reflection angle are different. However, the invention is not limited to the above-described configuration, but for example, as in a three-dimensional image inspection device 200 shown in FIG. 7 as a second embodiment, the first head part 2A and the second head part 2B can be disposed such that the first reflection angle and the second reflection angle are almost equal, and the first incident angle and the second incident angle are different.

(Adjustment of Fixed Position)

Figure 8:
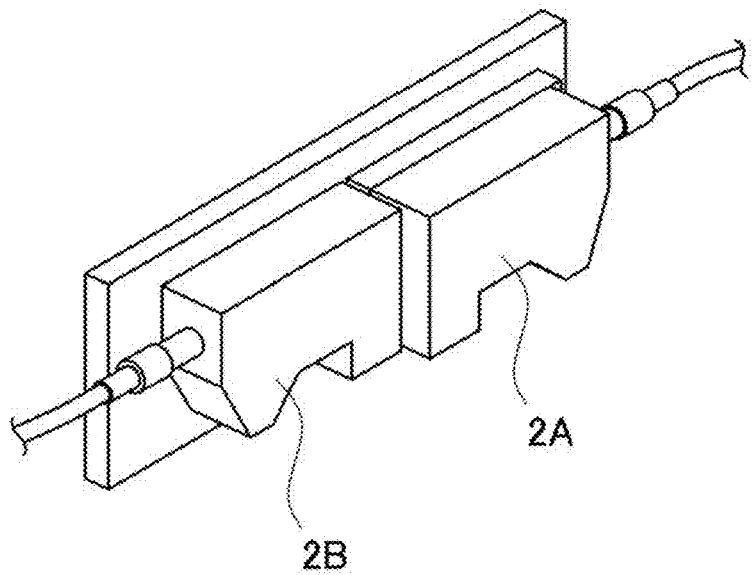
FIG. 8 is a perspective view showing a posture in which a first light projecting part and a second light projecting part are fixed.
Figure 9:
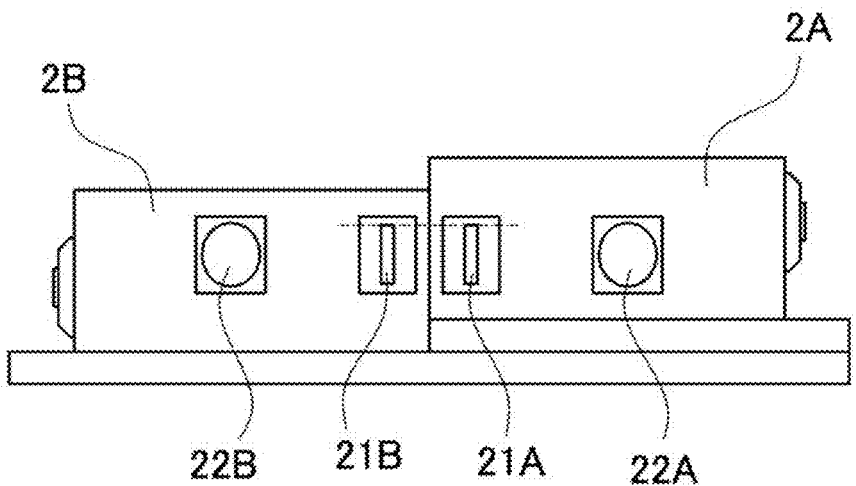
FIG. 9 is a bottom view showing a fixed state of the first light projecting part and the second light projecting part in FIG. 8.

As described later, a first height image and a second height image captured and generated by the first head part 2A and the second head part 2B are composed to generate a height composed image. In the generation of the height composed image, the first height image and the second height image need to be superimposed beforehand. For the superimposition, the first head part 2A and the second head part 2B need to be aligned and installed so that the same image of the inspection object can be captured in the first height image and the second height image. Thus, the first head part 2A and the second head part 2B are closely attached and disposed in a posture opposed to each other, as shown in FIG. 8. At this time, fixed positions of casings of the first head part 2A and the second head part 2B are adjusted so that the first light projecting part and the second light projecting part are located at same right and left positions in a horizontal plane, as shown in a bottom view of FIG. 9.

(Position Adjustment Parameters)

When the first head part 2A and the second head part 2B are fixed, adjustment is performed so as to prevent deviation in a coordinate position of each of the head parts from being caused as much as possible. That is, since positions of the light projecting parts and the light receiving parts have individual differences attributed to manufacturing tolerance between the head parts, physical work to calibrate these is required. As the position adjustment parameters for adjusting a relative positional relation between the head parts, six position adjustment parameters in the X-axis direction, the Y-axis direction, the Z-axis direction, an RX, which is a rotation direction in the X-axis direction, RY, which is a rotation direction in the Y-axis direction, and RZ, which is a rotation direction in the Z-axis direction, can be cited. Not all of these six position adjustment parameters need be used, but, for example, of these parameters, one or a plurality of position adjustment parameters can be deleted, which can simplify processing as well.

A relative positional relation between the first head part 2A and the second head part 2B causes the deviation in coordinate position, and affects measurement accuracy. On the other hand, it is not easy to completely adjust a deviation amount only by adjusting the installation positions of the first head part 2A and the second head part 2B. Consequently, the deviation amount of the first height image and the second height image captured and generated by the first head part 2A and the second head part 2B is calculated, and the first head part 2A and the second head part 2B are moved and rotated by this deviation amount and a deviation angle to superimpose the first height image and the second height image.

Here, one example of a procedure in which the height images (the first height image and the second height image) obtained by the plurality of head parts (the first head part 2A and the second head part 2B) are composed to generate the height composed image will be described. Generally, as shown in a flowchart of FIG. 10 and a data flow diagram of FIG. 11, three-dimensional search (step S161), superimposition processing of the height images (step S162), and composition processing of the height images (step S163) are required. That is, first, in step S161, in order to superimpose the first height image and the second height image, the three dimensional search is conducted to calculate the deviation amount of the first height image to the second height image, in other words, movement amounts for moving the first height image and the second height image so as to superimpose the same (the position adjustment parameters). When the deviation amount is found, the first height image and the second height image are subsequently moved by this deviation amount to be superimposed in step S162. The superimposed first height image and second height image are composed and integrated to obtain the height composed image.

Here, as to the three-dimensional search in step S161, a calculation cost is large, and if arithmetical operation is performed every operation time of the three-dimensional image inspection, a processing amount becomes enormous. That is, it is not efficient to arithmetically operate and calibrate the deviation in the coordinate position of the first height image and the second height image every superimposition, because a calculation amount is enormous.

(Three-Dimensional Calibration)

Consequently, three-dimensional calibration is performed prior to the operation of the three-dimensional image inspection, and the deviation amount of the first height image and the second height image obtained by the first head part 2A and the second head part 2B is stored in the position adjustment parameter storage region 31f of the storage part 31 as correction values, that is, the position adjustment parameters (calibration data), so that these position adjustment parameters are read and utilized at the operation time, which can accelerate the processing at the operation time. Specifically, the position adjustment parameters that prescribe a correspondence relation in a coordinate space between the first three-dimensional data generated with measurement values of the first light projecting/receiving part, and the second three-dimensional data generated with measurement values of the second light projecting/receiving part are beforehand created to be stored in the position adjustment parameter storage region 31*f* of the storage part 31. At the operation time, the position adjustment parameters are referred to as the correction values to correct the data.

Figure 12:
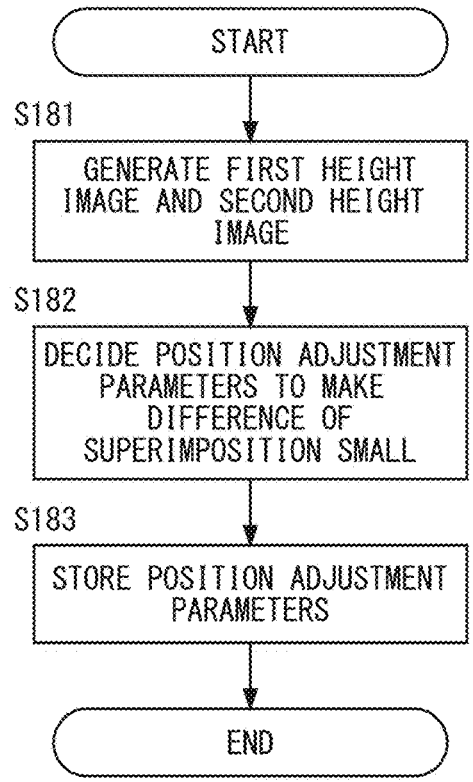
FIG. 12 is a flowchart showing a procedure of three-dimensional calibration.

One example of the above-described three-dimensional calibration will be described with reference to a flowchart of FIG. 12. First, in step S181, a workpiece as the inspection object is imaged by the first head part 2A and the second head part 2B at the operation time. The first height image and the second height image are generated from the three-dimensional data generation part from the images captured by the respective head parts.

Next, in step S182, the obtained first height image and second height image are superimposed, and the position adjustment parameters are decided so that a difference is smaller. Here, the deviation in a lateral direction (the X-axis direction), the deviation in a longitudinal direction (the Y-axis direction), the deviation in the height direction (the Z-axis direction) and the like are arithmetically operated. This allows the movement amounts in which the first height image and the second height image are to be moved at the superimposition time to be arithmetically operated.

Next, in step S183, the obtained movement amounts are stored in the position adjustment parameter storage region 31*f* of the storage part 31 as the correction values (the position adjustment parameters) at the operation time.

In this manner, the deviation amount of the first light projecting/receiving part and the second light projecting/receiving part is stored as the positional adjustment parameters prior to the operation of the three-dimensional image inspection, by which the three-dimensional data can be composed at the operation time, based on this deviation amount, so that an advantage of accelerating the processing at the operation time can be attained. Moreover, whether large deviation exists can be checked at the installation time.
(Simplified Height Image Composition Procedure)

Figure 10:
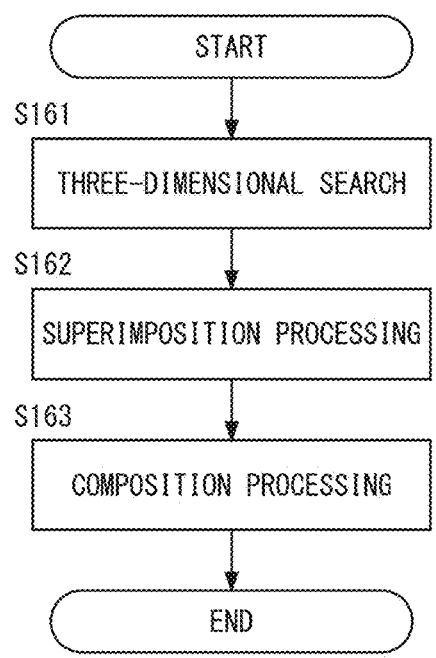
FIG. 10 is a flowchart showing a procedure for composing a first height image and a second height image to generate a height composed image.
Figure 11:
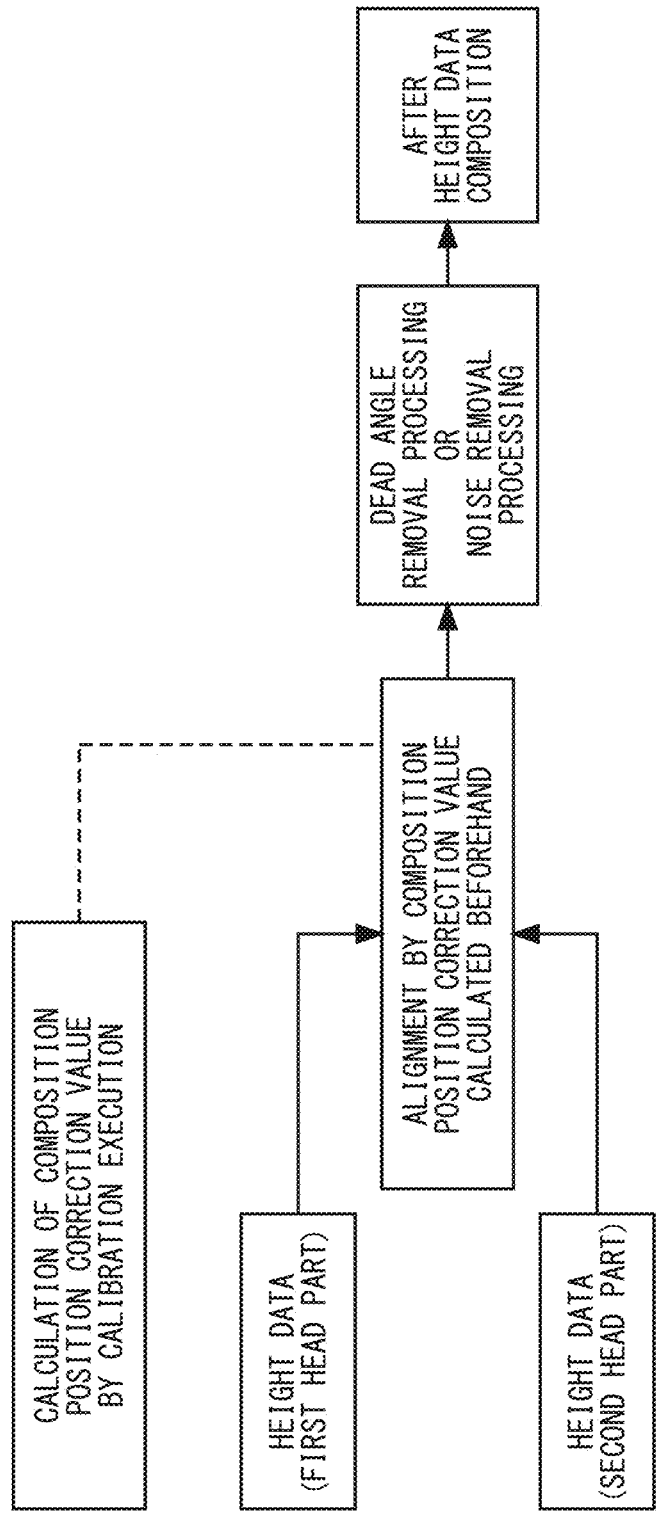
FIG. 11 is a data flowchart showing generation of the height composed image in FIG. 6A.
Figure 13:
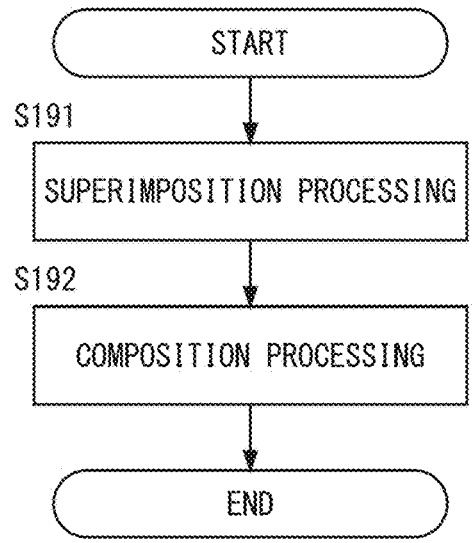
FIG. 13 is a flowchart showing a simplified procedure for generating the height composed image.

In this manner, the three-dimensional calibration is beforehand performed, the above-described three-dimensional search (step S161) in the flowchart of FIG. 10 can be omitted at the operation time. The simplified generation procedure of the height composed image will be described with reference to a flowchart of FIG. 13.

First, in step S191, the first height image obtained by the first head part 2A and the second height image obtained by the second head part 2B are superimposed by the composed image generation part 32*f*. For example, any one of the first height image or the second height image is fixed and the other is moved. For the movement amounts, the position adjustment parameters are read from the position adjustment parameter storage region 31*f* to be utilized. In step S192, the composition processing of the height image is performed.

In the specification, an example will be described in which using the first head part 2A by the optical cutting method shown in FIG. 1, the height image obtained by composing the two-dimensional profile images obtained by the optical cutting method is used. In the specification, examples of the measurement light and the reflected light include visible light, infrared light, ultraviolet light.

While in the example of FIG. 1, the configuration is employed, in which the first head part 2A and the second head part 2B are physically separated, the present invention is not limited to this configuration, and for example, the configuration may be such that the first head part 2A and the second head part 2B are integrated. Further, the configuration can also be such that the first head part and the second head part are integrated with the controller part. On the contrary, while in the configuration in FIG. 1, the first light projecting part 21A and the first light receiving part 22A are incorporated in the first head part 2A, the invention is not limited to this configuration, but the configuration may be such that the first light projecting part and the first light receiving part are disposed individually. Alternatively, the two-dimensional profile generation part may be disposed on the controller part side, and the three-dimensional data generation part may be provided on the head part side. Moreover, in FIG. 1, the respective head parts are connected to connectors for the head of the controller part 3 through cables. However, these are not limited to wired connection, but wireless connection is also available. Moreover, network connection through a communication protocol may be used.
(Dead Angle)

Figure 14:
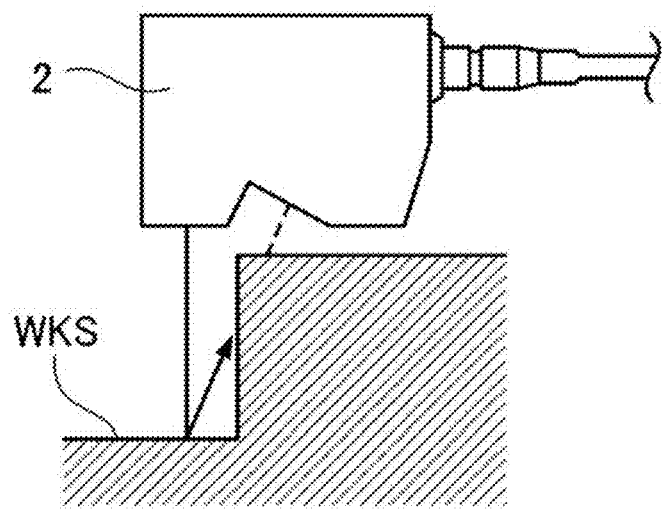
FIG. 14 is a cross-sectional view showing how a dead angle is caused when the workpiece is observed.

In the principle of triangulation, angles of the light projection and light reception are set to about 20° to 30°. Thus, as shown in FIG. 14, if a steep inclined plane exists in a workpiece WKS of the inspection object, there is caused a "dead angle" where the three-dimensional data cannot be properly acquired even when the image is captured by the head part 2. In pixels in this dead angle, erroneous height data may be measured. For example, if the workpiece is imaged by one head part to obtain the height image, an acute needle-like noise as indicated by arrow in FIG. 15 appears.

Figure 15:
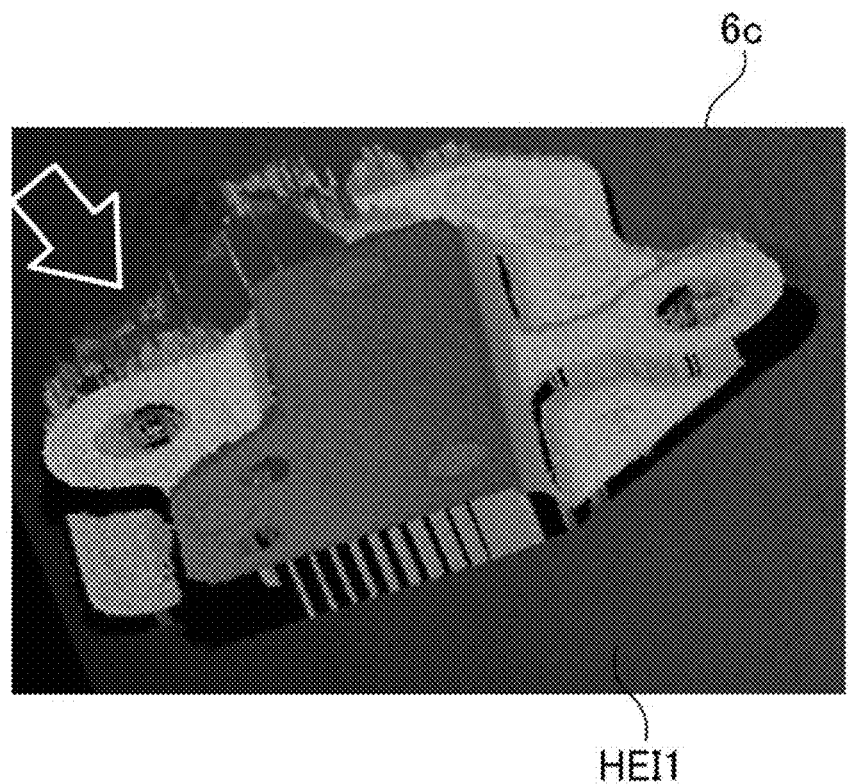
FIG. 15 is an image view showing the first height image generated by imaging the workpiece by a first head part.
Figure 16:
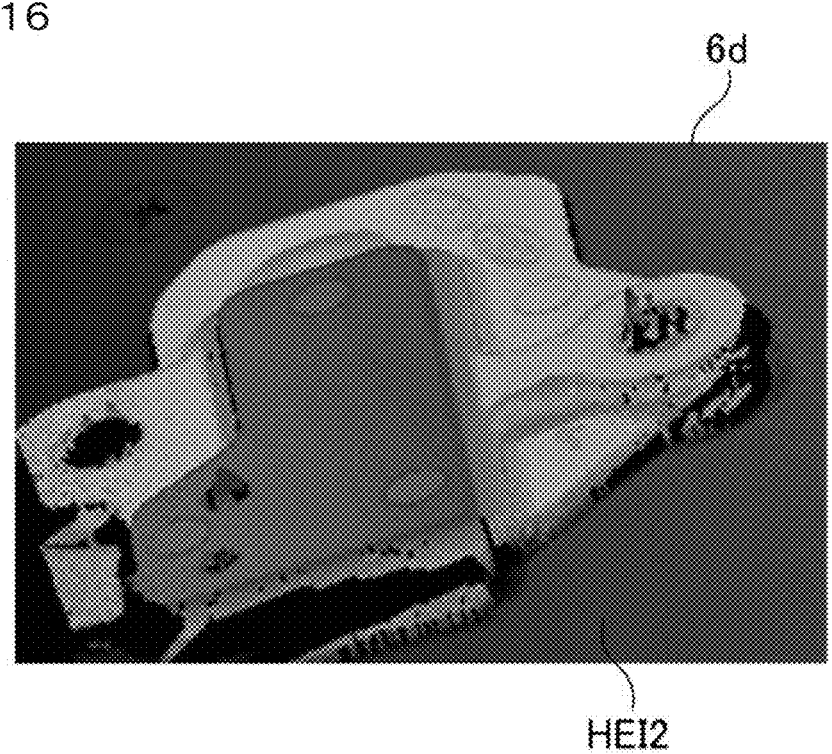
FIG. 16 is an image view showing the second height image generated by imaging the workpiece by a second head part.
Figure 17:
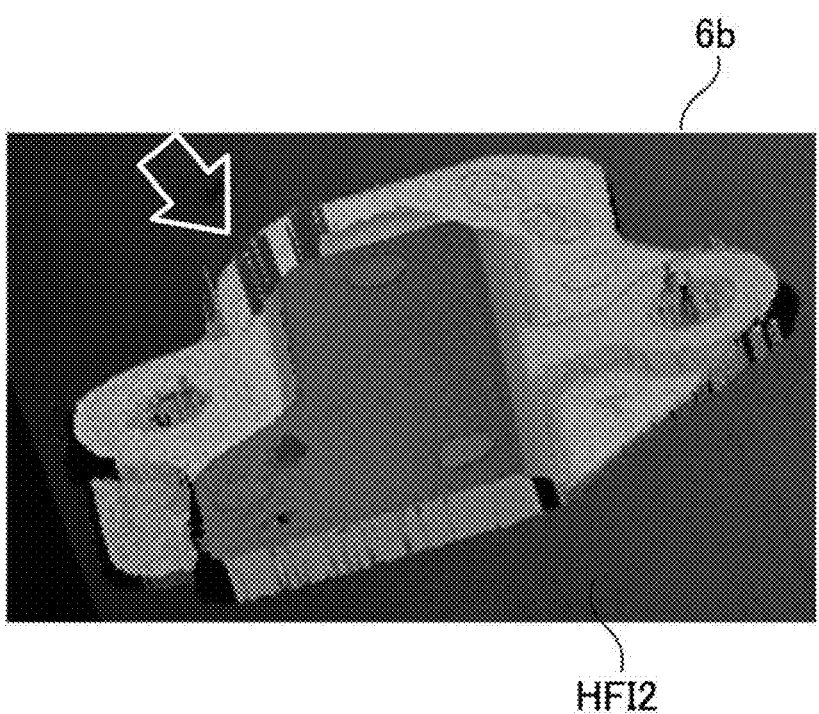
FIG. 17 is an image view showing the height composed image obtained by composing the height images in FIGS. 15 and 16.

In order to solve this, the height images observed from different angles by the two head parts are obtained as shown in FIG. 1, and information of the pixels in the dead angle is obtained from corresponding pixels of the height image captured by the other head part. For example, if a first height image HEI1 captured and generated by the first head part 2A is an image as shown in FIG. 15, and on the other hand, a second height image HEI2 captured and generated by the second head part 2B is an image as shown in FIG. 16, these height images are composed by the three-dimensional data generation part to obtain a height composed image HFI2 shown in FIG. 17 as the three-dimensional composed image. In comparison between the first height image HEI1 in FIG. 15 and the height composed image HFI2 in FIG. 17, the noise portion indicated by arrow in FIG. 15 is largely reduced in FIG. 17, and it can be confirmed that the pixels that are in the dead angle in the observation by the first head part 2A, so that the height information cannot be obtained are given the height information by the second head part 2B.

Figure 18:
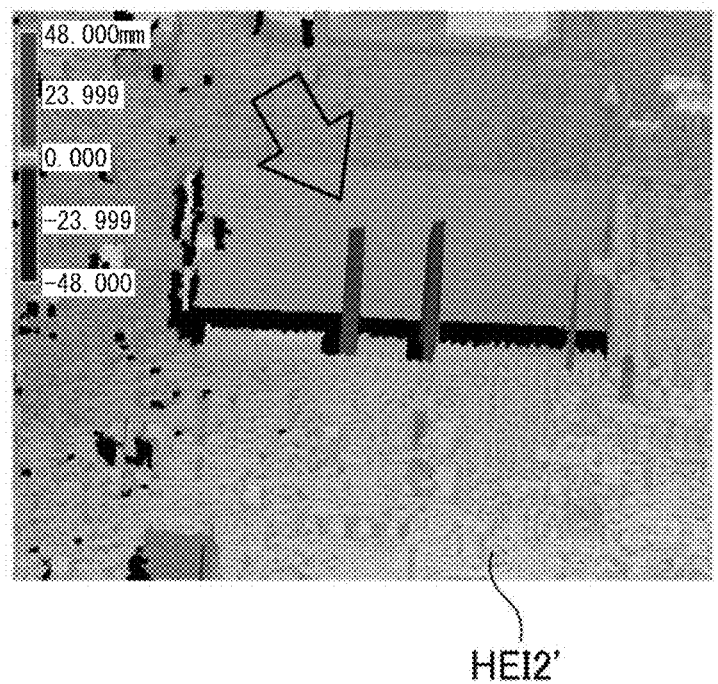
FIG. 18 is an image view showing the second height image generated by imaging a different workpiece by the second head part.
Figure 19:
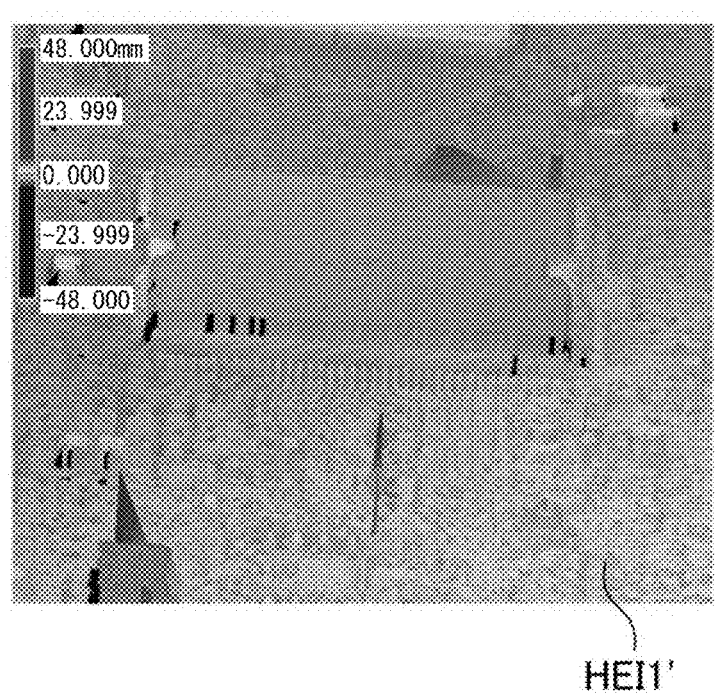
FIG. 19 is an image view showing the second height image generated by imaging the different workpiece by the first head part.
Figure 20:
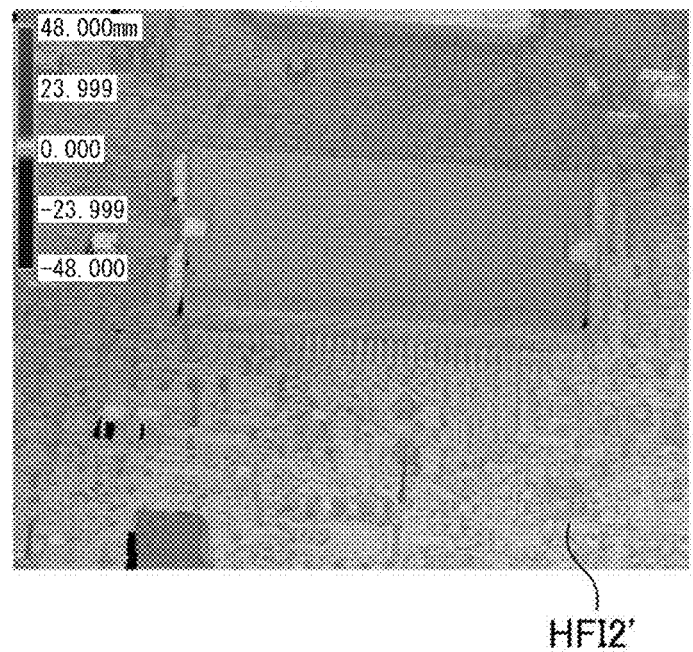
FIG. 20 is an image view showing the height composed image obtained by composing the height images in FIGS. 18 and 19.

Obviously, a reverse case is possible, that is, a region that becomes the dead angle from the second head part can be secured by the first head part 2. For example, a different workpiece is imaged by the second head part 2B, and a generated second height image HEI2' is shown in FIG. 18. While as indicated by arrow in this figure, peak-shaped erroneous detection is caused at two portions, in a first height image HEI1' captured and generated by the first head part 2A, the above-described erroneous detection cannot be observed in the relevant portions, as shown in FIG. 19. Consequently, when these height images are composed to generate a height composed image HFI2' by the composed image generation part 32*f*, the height image in which a region of mustache-like noise pertaining to the erroneous detection is reduced, as shown in FIG. 20 can be obtained.
(Image Composition Function)

The above-described image composition function of composing the plurality of height images is implemented by the composed image generation part 32*f*. The image composition function can be turned ON/OFF.

(Height Composed Image Condition Setting)

Figure 21:
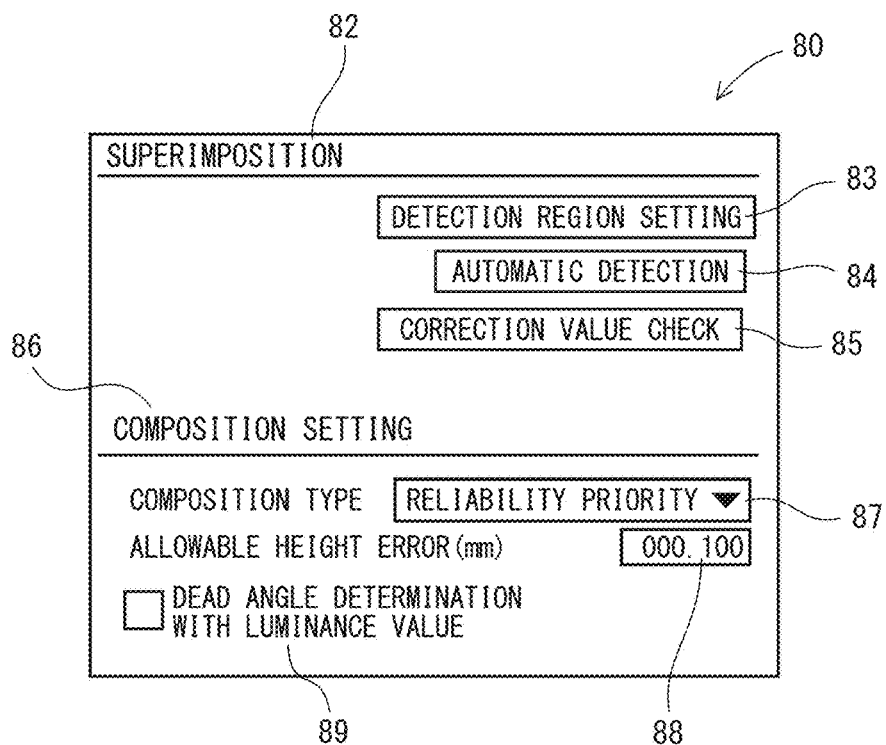
FIG. 21 is an image view showing a user interface screen of a height composed image condition setting screen in an operation program of the three-dimensional image inspection device.

For the superimposition processing and the composition processing performed by the image composition function, detailed setting can also be adjusted on the user side. One example of a user interface screen of a height composed image condition setting screen 80 for adjusting parameters of the above-described height composed image is shown in FIG. 21. In this figure, a superimposition condition setting field 82 to set a condition of the superimposition processing is provided in an upper stage, and a height image composition condition setting field 86 to set a condition of the height image composition processing is provided in a lower stage. In the superimposition condition setting field 82, a "detection region setting" button 83, a "superimposition execution" button 84, and a "correction value check" button 85 are provided.

The "detection region setting" button 83 is a member to set a detection region used in the superimposition processing. This detection region is set to include a characteristic shape of the workpiece, which will be a reference of the superimposition. Preferably, a non-planar portion having irregularity in the workpiece is selected. Alternatively, when an image of the workpiece disposed on the workpiece conveyance mechanism such as a conveyer is captured, designation is performed so that not the workpiece conveyance mechanism but the workpiece is included. Pressing the "detection region setting" button 83 allows a detection region setting screen to be displayed, and the setting of the detection region set currently is indicated by a coordinate position. By editing the coordinate position, the detection region can be modified. Moreover, pressing a "drawing" button 91 allows the detection region to be displayed on the height image in a superimposed manner. The detection region may be configured to be manually set by the user, or may be configured such that three-dimensional image inspection device automatically extracts the detection region from the height image. While in this example, the detection region is designated as a rectangular region, the shape is not limited to this rectangular shape, but can be any geometric figure such as a circle, or can also be an extracted shape such as an irregular shape of the workpiece.

The "superimposition execution" button 84 provided in the superimposition condition setting field 82 in FIG. 21 is a member to execute three-dimensional calibration. When the "superimposition execution" button 84 is pressed, the three-dimensional calibration is executed and the position adjustment parameters are arithmetically operated. That is, the movement amounts for the superimposition of the first height image and the second height image are arithmetically operated automatically, and the obtained movement adjustment parameters are stored in the storage part 31.

The "correction value check" button 85 is a member to check and modify the movement adjustment parameters as the correction values. Pressing the "correction value check" button 85 allows a correction value display screen to be displayed. In the correction value display screen, the position adjustment parameters obtained by the execution of the above-described three-dimensional calibration are displayed. For example, an X offset is displayed as the position adjustment parameter in the X-axis direction with a pixel number, a Y offset is displayed as the position adjustment parameter in the Y-axis direction in a pixel number, and a Z offset is displayed as the position adjustment parameter in the Z-axis direction in millimeter. The user can check these position adjustment parameters from the correction value display screen, and can modify these position adjustment parameters as needed.

On the other hand, in the height image composition condition setting field 86 provided in the height composed image condition setting screen 80 in FIG. 21, as the composition mode selection part 75, a "composition type" selection field 87, an "allowable height error" setting field 88, a "dead angle determination with luminance value" setting filed 89 and the like are provided. Details of these will be described later.

(Height Image Composition Algorism)

Here, height image composition algorism for the composed image generation part 32f to compose the first height image and the second height image will be described. In this example, the image composition processing is performed in accordance with the composition mode selected by the composition mode selection part 75.

(Composition Mode Selection Part 75)

The composition mode selection part 75 enables the first composition mode and the second composition mode to be selected. The first composition mode is a composition mode in which when the composed image generation part 32f generates the three-dimensional composed image, which is generated based on the three-dimensional data measured by both the first light projecting/receiving part and the second light projecting/receiving part with respect to respective pixels configuring the three-dimensional composed image. The first composition mode is a mode giving priority to reliability, and can be preferably utilized as noise removal processing.

On the other hand, the second composition mode is a composition mode in which the three-dimensional composed image is generated based on the three-dimensional data measured by any one or both of the first light projecting/receiving part and the second light projecting/receiving part. The second composition mode is a mode giving priority to measurement, and can be preferably utilized as dead angle removal processing. The user is enabled to select these composition modes, by which the user can select to which of the measurement in the dead angle region or the reliability of the measurement values priority is given in accordance with the workpiece, the inspection purpose and types, or the like. Especially, in addition to the measurement priority mode in which the pixels that cannot be measured by one of the light projecting/receiving parts due to the dead angle or the like are complemented by the three-dimensional data that can be measured by the other light projecting/receiving part, with respect to the pixels measured by both the light/receiving parts as well, the three-dimensional data having high reliability is preferentially used, which can implement the three-dimensional image inspection enhanced in reliability of the measurement.

As one aspect of the composition mode selection part 75 that performs the selection between the above-described composition modes, in the user interface screen of an operation program of the three-dimensional image inspection device shown in FIG. 21, the "composition type" selection field 87 provided in the height image composition condition setting field 86 is disposed. From the "composition type" selection field 87, the composition mode is selected, for example, from a drop-down list. For example, reliability priority, measurement priority, height difference measurement, or the like can be selected. The reliability priority is the reliability priority mode (the first composition mode), and is suitable for a case where the height composed image with less noise is desired. Moreover, the measurement priority is the measurement priority mode (the second composition mode), and is suitable for a case where the height composed image with a smaller dead angle is desired.

Further, the height measurement can be utilized in a case where an error of the calibration is desired to be checked or the like.

(Measurement Priority Mode)

In the measurement priority mode, its object is mainly to reduce the dead angle. In this composition mode, the respective corresponding pixels of the first height image and the second height image are measured as closely logical OR. That is, in the case of an invalid pixel in one of the height images, the corresponding pixel is used from the other height image. In this manner, the processing is performed so that the measurement values are obtained in as many pixels as possible. If the pixel values are not obtained in the two height images (the height information), this pixel is determined to be invalid. Meanwhile, if the pixel values are obtained in both the two height images, for example, these values are averaged. According to this composition mode, with respect to the mustache-like noise attributed to the dead angle in one of the height images, a removal effect can be obtained.

According to the measurement priority mode, the dead angle can be reduced. While it is difficult to eliminate the dead angle caused in principle by only one scanning by the one head part, using the plurality of head parts can largely reduce the dead angle by only one scanning.

(Reliability Priority Mode)

On the other hand, in the reliability priority mode, noise can be expected to be reduced. In this composition mode, the respective corresponding pixels of the first height image and the second height image are measured as closely logical AND. That is, in the case of the invalid pixel in one of the height images, it is determined to be an invalid pixel. The invalid pixel is painted out in black as a region where the height measurement is disabled, when the height composed image is displayed in the display part 6.

(Height Difference of Height Information)

In this composition mode, processing is performed so that the pixels having high reliability are left, in other words, so that the pixels having low reliability are excluded. Here, whether or not sufficient reliability is obtained is determined, based on a height difference of the obtained height information. Specifically, if the height difference between heights measured in the corresponding pixels of the first height image and the second height image exceeds an allowable range, this pixel is determined to be an invalid pixel. This setting is performed in the "allowable height error" setting field 88 provided in the height image composition condition setting field 86 of the height composed image condition setting screen 80 in FIG. 21. Here, as the allowable height error, the user designates the allowable height difference. This "allowable height error" setting field 88 becomes valid only when the reliability priority mode is selected.

Moreover, when the pixel values are obtained in the two height images, the pixel values are simply averaged. Alternatively, referring to information of a luminance image described later, the pixel having high reliability can be used, or a weighted average can also be taken.

If the pixel is determined to be the invalid pixel, the pixel value presumed from peripheral pixel values can also be inputted. For example, a value obtained by averaging the peripheral pixel values is designated as the pixel value for the relevant invalid pixel.

Figure 22:
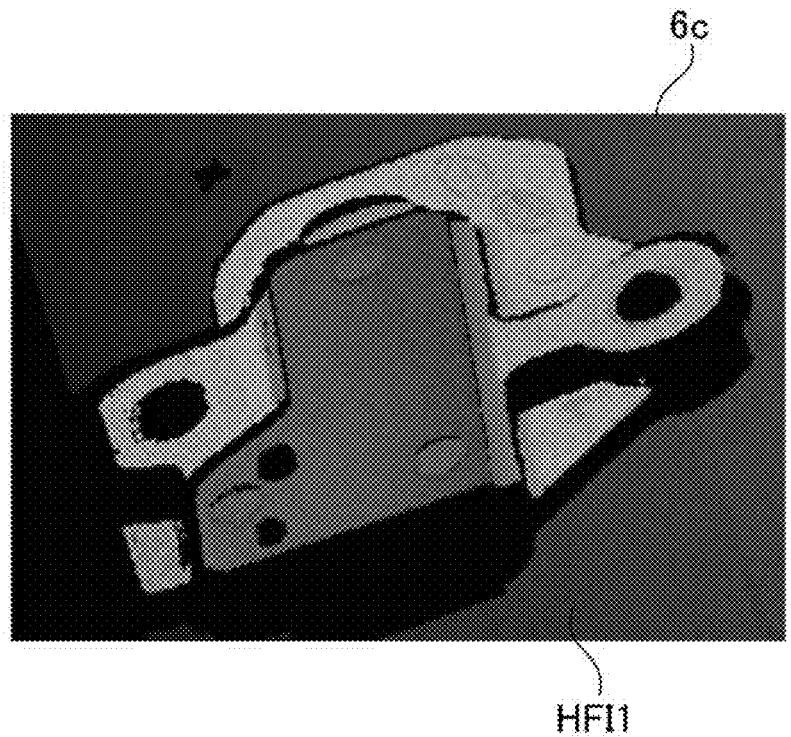
FIG. 22 is an image view showing the height composed image obtained by composing the height images in FIGS. 15 and 16 in a reliability priority mode with respect to the workpiece.
Figure 23:
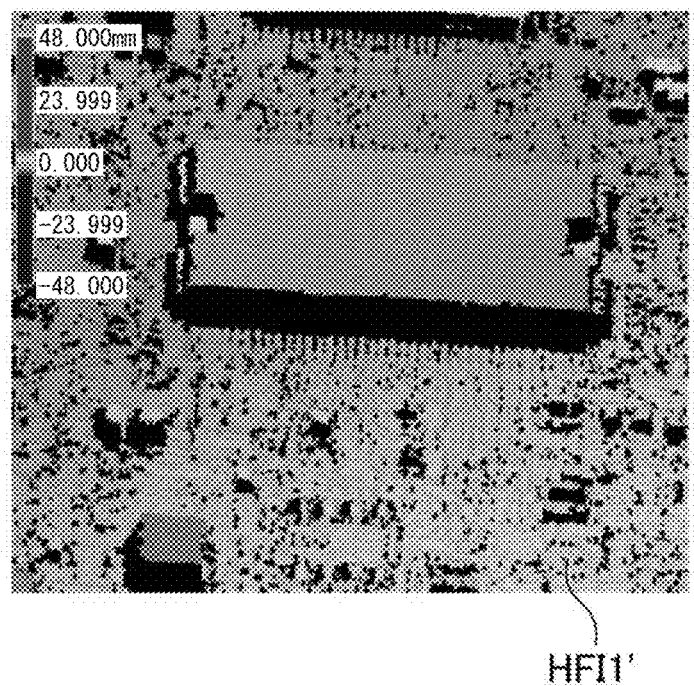
FIG. 23 is an image view showing the height composed image obtained by composing the height images in FIGS. 18 and 19 in the reliability priority mode with the different workpiece.

According to the reliability priority mode, the mustache-like noise can be easily removed. As one example, a height composed image HFI1 obtained by composing, in the reliability priority mode, the first height image HEI1 and the second height image HEI2 in FIGS. 15, 16 obtained with respect to the workpiece is shown in FIG. 22. As is evident in comparison with FIG. 17, it can be confirmed that the mustache-like noise is strongly removed. Similarly, a height composed image HFI1' obtained by composing, in the reliability priority mode, the first height image HEI1' and the second height image HEI2' in FIGS. 18, 19 obtained with respect to the different workpiece is shown in FIG. 23. In this example as well, as compared with FIG. 18 or the like, it can be understood that the mustache-like noise is removed. Conventionally, in order to make the mustache-like noise invalid pixels, various types of filter processing and tuning of setting have been required. However, the height images using the plurality of head parts are combined, which allows the easy removal of the mustache-like noise to be expected. Moreover, this configuration is easily implemented, and no knowledge regarding filters or the like is required, which can bring about an advantage that even a beginner can easily utilize the device.

(Acquisition of Luminance Image)

Figure 24:
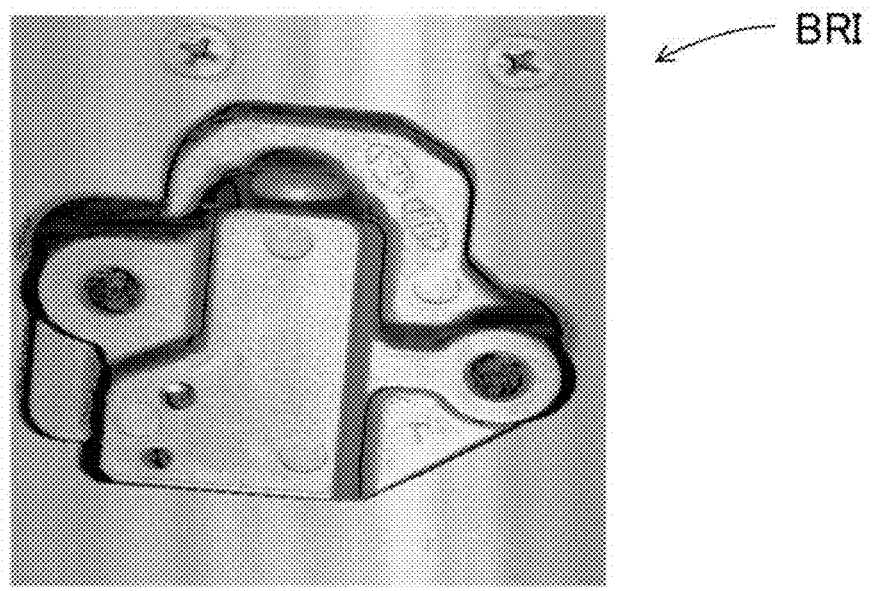
FIG. 24 is an image view showing a generated luminance image.

Moreover, the three-dimensional image inspection device acquires the above-described three-dimensional data, and meanwhile, the luminance information in which each pixel is represented by luminance information of a surface of the workpiece can also be acquired. Utilizing this luminance information, a luminance image can also be generated. The above-described generation of the luminance image is performed by the luminance image generation part 32g. One example of a luminance image BRI generated by the luminance image generation part 32g is shown in FIG. 24.

Here, one example of a procedure in which the luminance image generation part 32g generates the luminance image will be described in comparison with the generation of the height image with reference to FIGS. 25A to 2511. Here, how the workpiece WK1 shown in FIG. 6A is imaged by the head parts 2 to generate the height image and the luminance image will be described.

The workpiece WK1 has a gray rectangular parallelepiped shape, and is placed on a white stand ST, as shown in FIG. 25A. This stand ST has one size larger plate shape than the workpiece WK1, and is placed on a black conveyer CV, which is one form of the workpiece conveyance mechanism 1, to be conveyed in the Y-axis direction. The laser beam LB is applied to the inspection object including the above-described workpiece WK1 in the X-axis direction at a scanning position SCN, and a light receiving image DEI obtained by receiving reflected light thereof in the light receiving element is as shown in FIG. 25B. In FIG. 25B, a pixel that can obtain the reflected light is represented by a white dot, and a region where the reflected light cannot be obtained is displayed in black. When with respect to the above-described light receiving image DEI, the two-dimensional profile indicating the height information at the scanning position SCN obtained by scanning the laser beam LB is acquired, the relevant two-dimensional profile is as shown in FIG. 25C. This two-dimensional profile 2DP is found at each of the scanning positions to compose these two-dimensional profiles, as shown in FIG. 25D, by which a height image HEI' can be obtained. The height image HEI' is represented, based on the height information in which luminance and hue are varied. In an example of FIG. 25E, the height image HEI' is displayed in monochrome so that a higher portion has a higher luminance. As a result, as shown in FIG. 25E, in the obtained height image HEI', since a portion of the workpiece WK1 is highest, this portion is displayed in white, and since the stand ST is second highest, this portion is displayed in gray, and finally, the conveyer CV is displayed in black.

On the other hand, a luminance image BRI' is generated by the luminance image generation part 32g as follows. First, a luminance profile BRP shown in FIG. 25F is generated from the light receiving image DEI in FIG. 25B. The luminance profile BRP is generated based on a magnitude of the luminance (brightness). That is, a gradation value of a peak of the light receiving image DEI is used to thereby obtain the luminance profile BRP indicating shade, i.e., the luminance. In the luminance profile BRP in FIG. 25F, the portion of the white stand ST is largest, the portion of the gray workpiece WK1 is the second large, and the portion of the conveyer CV is the smallest. The luminance profile BRP obtained in this manner is held in storage part 31. Further, the luminance profile BRP is generated from the light receiving image DEI obtained at each of the scanning positions to be held in the storage part 31, and the obtained luminance profiles BRP are composed, as shown in FIG. 25G to generate a luminance image BRI'. The luminance image BRI' obtained from FIG. 25A is shown in FIG. 25H. In the luminance image BRI' shown in this figure, similar to FIG. 25A, the workpiece WK1 is displayed in gray, the stand ST is displayed in white, and the conveyer CV is displayed in black.

In this manner, when the two-dimensional profiles indicating the height information are disposed side by side, the height image HEI' is obtained, and when the luminance profiles BRP indicating the shade information are disposed side by side, the luminance image BRI' is obtained. In the above-described example, while, for convenience of the description, the generation procedures of the height image HEI' and the luminance image BRI' have been described individually, actually, the generations of these height image HEI' and the luminance image BRI' can also be simultaneously performed in parallel, or the height image HEI' and the luminance image BRI' can be sequentially generated. The generation order in this case does not matter.

Moreover, the first luminance data obtained by the first light projecting/receiving part and the second luminance data obtained by the second light projecting/receiving part can also be composed to generate the luminance composed image. In this manner, for the luminance image as well, by composing the luminance data obtained from different angles, the luminance composed image having less defect in which the portion in the dead angle is compensated by the other light projecting/receiving part can be obtained, and the outer appearance inspection using the above-described luminance composed image can be performed. The above-described generation of the luminance composed image is performed, for example, by the luminance image generation part 32g.

(Dead Angle Determination Utilizing Luminance Information)

Further, the obtained luminance information can be utilized as an index indicating reliability of each of the pixels at the execution time of the image composition function. For example, in the user interface screen of the operation program of the three-dimensional image inspection device shown in FIG. 21, if a check box of the "dead angle determination with luminance value" setting field 89 is turned ON, the dead angle determination using the luminance information is performed. When the dead angle determination using the luminance information is performed, the pixel in a portion of the dead angle has no luminance, and is displayed in black. Thus, a black portion in the luminance image is determined to be the dead angle, and the pixel determined to be the dead angle is excluded at the execution time of the image composition function, which can implement the image composition enhanced in reliability.

Moreover, a configuration may be such that if a difference between the luminance values of the corresponding pixels is larger than a predetermined threshold, it is determined that the reliability of the three-dimensional data of the pixel having the smaller luminance value is low. That is, similar to the height difference of the above-described height information, if the luminance values are obtained largely differently between the two luminance images, it is predicted that any of the luminance values is inaccurate, so that the reliability of this pixel is considered to be low.

Further, a height of the luminance value and a height of the reliability may be associated with each other. For example, a configuration can be such that, if the pixel values are obtained from both corresponding pixels of the first height image and the second height image, the higher luminance value is employed and the lower luminance value is deleted. Alternatively, in place of completely excluding the information of the pixel having the lower luminance value, weighting may be applied. For example, when the pixel having the luminance value 100 and the pixel having the luminance value 60 are composed, for the luminance value 100, the weighting is set to 100%, and for the luminance value 60, the weighting is set to 10% to arithmetically operate the luminance value of the height composed image.

Here, with respect to the inspection object with the workpiece WK1 placed on the stand ST shown in FIG. 25A, the height images and the luminance images are generated by the first head part 2A and the second head part 2B, and the height composed images are generated in the measurement priority mode and the reliability priority mode, based on these images. How the above-described generation is performed will be described with reference to FIGS. 26A to 26F. First, a second height image HEI2" obtained by the second head part 2B is shown in FIG. 26A, and a second luminance image BRI2" is shown in FIG. 26B. Since as shown in FIG. 2, the second head part 2B observes the inspection object from a left side, in FIGS. 26A, 26B, the dead angle, that is, a shadow is caused on a right side. Regions of the shadow are each indicated by oblique line in the figures as an invalid image in which the height information cannot be detected. As shown in the second height image HEI2" in FIG. 26A, noise is caused in a second region A2 on the upper left of the stand ST (indicated by circles in the figure). In the second luminance image BRI2" in FIG. 26B, the corresponding second region A2 is displayed a little darker (indicated in a sand-like manner in the figure). With respect to the pixels in the second region A2, since the height information is obtained in the second height image HEI2", the pixels are not invalid pixels but valid pixels. However, since the luminance is low in the second luminance image BRI2", the pixels are treated as pixels having low reliability.

On the other hand, a first height image HEI1" and a first luminance image BRI1" obtained by the first head part 2A are shown in FIGS. 26C, 26D, respectively. Since as shown in FIG. 2, the first head part 2A observes the inspection object from a right side, the dead angle is caused on a left side in each of the images, and is displayed as a shadow. In the first height image HEI1" of FIG. 26C, noise is caused in a first region A1 on the upper right of the stand ST with the workpiece WK1 disposed (indicated by circles in the figure), and similarly, in the first luminance image BRI1" of FIG. 26D, the corresponding first region A1 is displayed a little darker (indicated in a sand-like manner in the figure). With respect to the pixels in the first region A1 as well, since the height information is obtained in the first height image HEI1", the pixels are not invalid pixels but valid pixels. However, since the luminance is low in the first luminance image BRI1", the pixels are treated as pixels having low reliability.

When the first height image HEI1" and the second height image HEI2" obtained in this manner are composed to obtain the height composed image, if the measurement priority mode is selected, a second height composed image HFI2" shown in FIG. 26E is obtained. Here, with respect to the second region A2 determined to have low reliability in the second luminance image BRI2", the height information is preferentially employed from the pixels in the corresponding region in the first height image HEI1" having higher reliability, and as a result, the noise is reduced and eliminated in the second region A2 indicated by broken line in the figure. Similarly, with respect to the first region A1 determined to have low reliability in the first luminance image BRI1" as well, the height information is preferentially employed from the pixels having high reliability in the corresponding region in the second height image HEI2", so that the noise is reduced or cut in the first region A1 indicated by broken line in the figure. Further, with respect to the pixels in the dead angle caused on the right side of the second height image HEI2" and in the dead angle caused on the left side of the first height image HEI1", the height information in the respective corresponding regions also is utilized from the pixels in the other height image to thereby obtain the height information with respect to the invalid pixels in the portions of the dead angle, so that the pixels become valid pixels. In this manner, in the second height composed image HFI2" composed in the measurement priority mode, the noise and the dead angle observed in the height image generated by one of the head parts can be removed.

On the other hand, a first height composed image HFI1" composed in the reliability priority mode is shown in FIG. 26F. In this first height composed image HFI1", in the second region A2, a difference between the height information obtained by the second height image HEI2" and the height information obtained in the first height image HEI1" is larger than a predetermined value, and thus, these pixels are determined to be invalid pixels. Similarly, in the first region A1 as well, a difference between the height information obtained in the first height image HEI1" and the height information obtained in the second height image HEI2" is larger than the predetermined value, and thus, these pixels are determined to be invalid pixels. As a result, the pixels in the second region A2 displayed as the noise in the second height image HEI2" are determined to be invalid pixels, and the pixels in the first region A1 displayed as the noise in the first height image HEI1" are also determined to be invalid pixels. Similarly, both the pixels in the region of the invalid pixels, which is the dead angle in the second height image HEI2", and the pixels in the region of the invalid pixels, which is the dead angle in the first height image HEI1", are also invalid pixels. In this manner, in the first height composed image HFI1", the invalid pixels are increased as compared with the second height composed image HFI2". In the first height composed image HFI1" obtained in the reliability priority mode, for example, in the case where a height on the stand ST is desired to be measured accurately, or the like, a measurement position is designated while excluding the pixels in the regions determined to be invalid pixels. In the above-described measurement purpose, even if there are many invalid pixels in the height composed image, the measurement is considered to have no problem, as long as the region having high reliability is obtained, and since the pixels having low reliability are excluded, the measurement accuracy is secured and usefulness is sufficiently secured.

With the above-described configuration, in addition to reduce the dead angle in the measurement priority mode, the reliability priority mode is provided, which can increase the measurement accuracy of the pixels that can be measured by both the head parts. Moreover, since without newly designing a dedicated head part including a plurality of light projecting/receiving parts, a plurality of existing laser displacement meters can be prepared and used as the head parts, the reduction of the dead angle and the enhancement of the measurement accuracy can be achieved while utilizing the existing system.

In the above-described example, the configuration has been described in which the two light projecting/receiving parts, that is, the first light projecting/receiving part and the second light projecting/receiving are used. However, in the invention, the number of the light projecting/receiving parts is not limited to two, but three or more light projecting/receiving parts may be provided. Moreover, the number of the head parts in each of which the light projecting/receiving part is provided is not limited, but a configuration may be such that each of the light projecting/receiving parts is provided in the individual head part, or such that a common head part contains the two or more light projecting/receiving parts.

A three-dimensional image inspection device and a three-dimensional image inspection method of the invention can be utilized in outer appearance inspection of a workpiece conveyed on a line.

What is claimed is:

1. A three-dimensional image inspection device for conducting outer appearance inspection, based on height information of an inspection object, the three-dimensional image inspection device comprising:

a first head part that applies measurement light to the inspection object at a first incident angle, and receives reflected light reflected from the inspection object at a first reflection angle;

a second head part that applies measurement light to the inspection object at a second incident angle, and receives reflected light reflected from the inspection object at a second reflection angle;

a three-dimensional data generation part configured to generate first three-dimensional data, based on first light receiving amount data obtained from the first head part, and generates second three-dimensional data, based on second light receiving amount data obtained from the second head part in accordance with a principle of triangulation;

a composed image generation part configured to compose the first three-dimensional data and the second three-dimensional data, and generate a three-dimensional composed image having information in a height direction;

a display part configured to display the three-dimensional composed image composed by the composed image generation part;

a composition mode selection from a user interface screen to enable selection of a first composition mode or a second composition mode when the composed image generation part generates the three-dimensional composed image, wherein the first composition mode is a reliability priority mode that determines a pixel of the composed image where both the first three-dimensional data and the second three-dimensional data are a valid pixel, and the second composition mode is a measurement priority mode that determines a pixel of the composed image where one of the first three-dimensional data or the second three-dimensional data is a valid pixel; and an inspection part configured to conduct the outer appearance inspection of the inspection object, based on the three-dimensional composed image composed by the composed image generation part.

2. The three-dimensional image inspection device according to claim 1, wherein the composed image generation part is configured to remove noise from the three-dimensional composed image in the first composition mode, or to remove dead angle from the three-dimensional composed image in the second composition mode.

3. The three-dimensional image inspection device according to claim 1, wherein the first incident angle and the second incident angle, or the first reflection angle and the second reflection angle are different angles.

4. The three-dimensional image inspection device according to claim 1, wherein each of the first head part and the second head part also outputs luminance information of the inspection object together with the three-dimensional data.

5. The three-dimensional image inspection device according to claim 4, wherein the luminance information is luminance profiles, and the luminance profiles can be joined to generate a luminance image.

6. The three-dimensional image inspection device according to claim 4, further comprising a luminance image generation part configured to compose first luminance data obtained by the first head part, and second luminance data obtained by the second head part and generates a luminance composed image.

7. The three-dimensional image inspection device according to claim 1, wherein the height information is obtained in both the corresponding pixels of the first three-dimensional data and the second three-dimensional data, and the composed image generation part averages the two pieces of height information.

8. The three-dimensional image inspection device according to claim 1, further comprising a storage part configured to store a position adjustment parameter that prescribes a correspondence relation in a coordinate space between the first three-dimensional data and the second three-dimensional data generated by the three-dimensional data generation part, wherein the composed image generation part composes the first three-dimensional data and the second three-dimensional data, based on the position adjustment parameter stored in the storage part, and generates the three-dimensional composed image having the information in the height direction.

9. The three-dimensional image inspection device according to claim 1, wherein the display part can display the first three-dimensional data and the second three-dimensional data side by side.

10. The three-dimensional image inspection device according to claim 1, wherein the three-dimensional composed image is a height image in which the information in the height direction is a pixel value of each of the pixels.

11. A three-dimensional image inspection method for conducting an outer appearance inspection, based on three-dimensional composed image having height information of an inspection object, the method comprising the steps of:

selecting from a user interface screen prompting a selection of a first composition mode in which noise removal processing of the three-dimensional composed image is performed or a second composition mode in which dead angle removal processing of the three-dimensional composed image is performed;

applying measurement light to the inspection object at a first incident angle, and receiving reflected light reflected from the inspection object at a first reflection angle by a first head part, and meanwhile, applying measurement light to the same inspection object at a second incident angle, and receiving reflected light reflected from the inspection object at a second reflection angle by a second head part, and in accordance with a principle of triangulation, generating first three-dimensional data, based on first light receiving amount data obtained from the first head part, and meanwhile, generating second three-dimensional data, based on second light receiving amount data obtained from the second head part;

when the first three-dimensional data and the second three-dimensional data are composed to generate a three-dimensional composed image having information in a height direction, in accordance with the selection of the first composition mode or the second composition mode, generating the three-dimensional composed image, based on the three-dimensional data measured by both the first head part and the second head part with respect to respective pixels configuring the three-dimensional composed image, when the first composition mode is selected, or generating the three-dimensional composed image, based on the three-dimensional data measured by one of the first head part and the second head part with respect to the respective pixels when the second composition mode is selected;

causing a display part to display the three-dimensional composed image composed by a composed image generation part; and conducting the outer appearance inspection of the inspection object, based on the composed three-dimensional composed image.

* * * * *